(12) United States Patent
De Cola et al.

(10) Patent No.: US 8,962,838 B2
(45) Date of Patent: Feb. 24, 2015

(54) PLATINUM COMPLEXES AND THEIR USE

(75) Inventors: Luisa De Cola, Strasbourg (FR); Matteo Mauro, Taurisano (IT); Nermin Seda Kehr, Muenster (DE); Cristian Alejandro Strassert, Muenster (DE)

(73) Assignee: Westfaelische Wilhelms-Universitaet Muenster, Munich (DE)

( * ) Notice: Subject to any disclaimer, the term of this patent is extended or adjusted under 35 U.S.C. 154(b) by 0 days.

(21) Appl. No.: 14/002,637

(22) PCT Filed: Mar. 1, 2012

(86) PCT No.: PCT/EP2012/053586
§ 371 (c)(1),
(2), (4) Date: Dec. 10, 2013

(87) PCT Pub. No.: WO2012/117082
PCT Pub. Date: Sep. 7, 2012

(65) Prior Publication Data
US 2014/0088307 A1 Mar. 27, 2014

(30) Foreign Application Priority Data
Mar. 1, 2011 (DE) .................. 10 2011 001 007

(51) Int. Cl.
*C07F 15/00* (2006.01)
*G01N 21/76* (2006.01)
*C07D 401/04* (2006.01)
*C07D 401/14* (2006.01)
*C09K 11/06* (2006.01)
*H05B 33/14* (2006.01)
*H01L 51/00* (2006.01)
*H01L 51/50* (2006.01)

(52) U.S. Cl.
CPC .......... *C07F 15/0093* (2013.01); *C07D 401/04* (2013.01); *C07D 401/14* (2013.01); *C09K 11/06* (2013.01); *H05B 33/14* (2013.01); *H01L 51/0087* (2013.01); *C09K 2211/1029* (2013.01); *C09K 2211/1044* (2013.01); *C09K 2211/1059* (2013.01); *C09K 2211/185* (2013.01); *H01L 51/5016* (2013.01)
USPC ............................................. 546/2; 436/172

(58) Field of Classification Search
USPC .......................................... 546/2, 3; 436/172
See application file for complete search history.

(56) References Cited

U.S. PATENT DOCUMENTS

2008/0309227 A1 12/2008 Che
2010/0314994 A1 12/2010 Che
2011/0262897 A1 10/2011 Williams

FOREIGN PATENT DOCUMENTS

| JP | 2007-169541 | 7/2007 |
| WO | 2007090343 | 8/2007 |
| WO | 2007133349 | 11/2007 |
| WO | 2009111299 | 9/2009 |
| WO | 2011050574 | 5/2011 |

OTHER PUBLICATIONS

Jia, Wen-Li et al.: Novel phosphorescent cyclometalated organotin and organolead complexes of 2,6-bis(2'-indolyl)pyridine and 2,6-bis[2'-(7-azaindolyl)] pyridine. Organometallics, vol. 22, pp. 4070-4078, 2003.*
Strassert C. A., Chien, C.-H., Galvez•Lopez, M. D., Kourkoulos, D., Hertel, D., Meerholz, K. And De•Cola, L. (2011), Lumineszenz eines Platin(II)-Komplexes in gelierenden Nanofasern and elektrolumineszierenden Filmen. Angew. Chem., 123: 976-980. doi: 10.1002/ange.201003818.
Duati et al.,Enhancennent of Luminescence of Lifetimes of Mononuclear Ruthenium(II)Terpyridine Complexes by Manipulation of the o-Donor Strength of Ligands, Inorganic Chemistry (Impact Factor: 4.6). Jan. 2004; 42 (25):8377-84. DOI:10.1021/ic034691m.
Schneider et al., Cyclometalated 6-phenyl-2,2'-bipyridyl (CNN) platinum(II) acetylide complexes: structure, electrochemistry, photophysics, and oxidative- and reductive-quenching studies, Inorg. Chem., 2009, 48 (10), pp. 4306-4316, DOI: 10.1021/ic801947v.
Rubino et al., Synthetic, structural and biochemical studies of polynuclear platinum(II) complexes with heterocyclic ligands, European Journal of Medicinal Chemistry vol. 44, Issue 3, Mar. 2009, pp. 1041-1048.
Mydlak et al.,Controlling aggregation in highly emissive Pt(II) complexes bearing tridentate dianionic NNN ligands. synthesis, photophysics, and electroluminescence, Chem. Mater., 2011, 23 (16), pp. 3659-3667.

\* cited by examiner

*Primary Examiner* — Charanjit Aulakh
(74) *Attorney, Agent, or Firm* — 24IP Law Group USA, PLLC; Timothy R DeWitt

(57) ABSTRACT

The invention relates to platinum complexes and their use in biomedical applications, like in vitro and in vivo imaging and cell staining. The present invention provides new materials and their use as imaging agent. The formation of luminescent aggregates can allow a switch of the emission leading to a dynamic label and on the formation of soft assemblies, which, in some cases, are even more emissive than the isolated corresponding species.

14 Claims, 13 Drawing Sheets

PLATINUM COMPLEXES AND THEIR USE

CROSS REFERENCES WITH OTHER APPLICATIONS

This application claims priority of German application DE 10 2011 001 007.6 filed Mar. 1, 2011, which is incorporated by reference herein.

FIELD OF THE INVENTION

The invention relates to platinum complexes and their use in biomedical applications, like in vitro and in vivo imaging and cell staining.

BACKGROUND

Cell staining is a technique that can be used to better visualize cells and cell components under a microscope. By using different stains, one can preferentially stain certain cell components, such as a nucleus or a cell-membrane, or the entire cell. Most stains can be used on fixed, or non-living cells, while only some can be used on living cells.

Electroluminescent compounds like platinum(II) complexes gained more and more attention recently. WO 2009/111299 discloses a platinum(II) complex in which three aromatic systems together form a tridentate ligand coordinated to a platinum ion through atoms X, Y and Z. The complexes are asymmetric and emit in the UV to near IR range. They are intended for use in organic light emitting devices.

Platinum complexes are also used in tumour therapy as they intercalate with DNA. This means that those complexes are toxic, which is a problem for their use in cell staining, especially in in vivo staining of cells.

BRIEF SUMMARY OF THE INVENTION

The object of the present invention is to provide novel platinum(II) complexes which are either toxic or not toxic and suitable to stain cells or cell compartments.

The invention provides a platinum(II) complex comprising a mono- or dinuclear N^N^N-type ligand according to one of formulas (I) or (II)

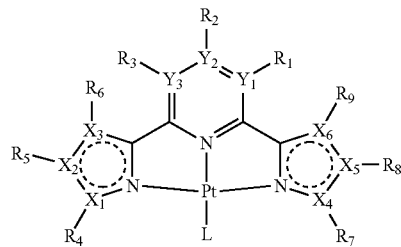

(I)

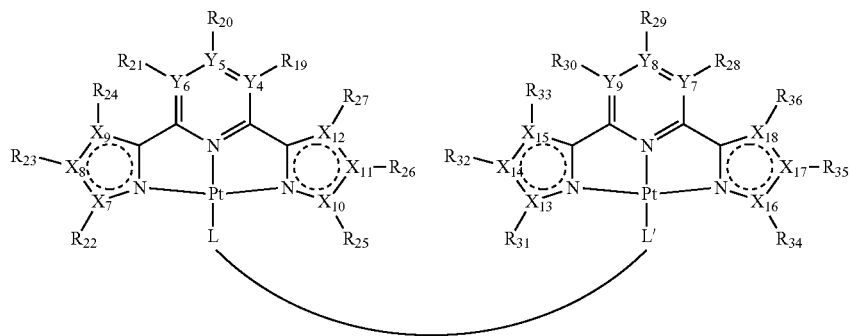

(II)

wherein $Y_1, Y_2, Y_3, Y_4, Y_5, Y_6, Y_7, Y_8$ and $Y_9$ can be independently either carbon or nitrogen with the proviso if $Y_1$ or $Y_4$ are a nitrogen atom, then $R_1$ or $R_{19}$ are absent;
if $Y_2$ or $Y_5$ are a nitrogen atom, then $R_2$ or $R_{20}$ are absent;
if $Y_3$ or $Y_6$ are a nitrogen atom, then $R_3$ or $R_{21}$ are absent;
if $Y_7$ is a nitrogen atom, then $R_{28}$ is absent;

if $Y_8$ is a nitrogen atom, then $R_{29}$ is absent;
if $Y_9$ is a nitrogen atom, then $R_{30}$ is absent,
and if $Y_1, Y_2, Y_3, Y_4, Y_5, Y_6, Y_7, Y_8$ and $Y_9$ represent a carbon $R_1, R_2, R_3, R_{19}, R_{20}, R_{21}, R_{28}, R_{29}$, and $R_{30}$ are selected from the group comprising H, F, Cl, Br, I, $CH_3$, $CF_3$, $NO_2$, OH, tiocyanate, isotiocyanate, —NCO, —CN, CHO, COOH, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, linear or branched, chiral or achiral, from 1 till 18 carbon atom containing any combination of the following groups: $CF_3$, $NO_2$, OH, CHO, COOH, tiocyanate, isotiocyanate, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, m aliphatic or alicyclic alkyl, alkenyl, alkynyl, aryl, ester, carboxy, amine, sulfoxide, amide, phosphine or neutral heterocyclic moieties such as ethyl, n-propyl, phosphine, n-Butyl, t-Butyl, iso-Propyl, Hexyl, $F(CF_2)_m(CH_2)_n$— (m=1-10, n=0-4), $F(CF_2)_m(CH_2)_nC_6H_4$— (m=1-10, n=0-4), $O(CH_2CH_2O)_nCH_3$ (n=0-10000), haloalkyl, mono- or, disulfide, natural or synthetic sugar residuals, biotin, phosphonium moiety, aminoacidic residual, antibody, Phenyl, Chlorophenyl, Tolyl, Anisyl, Trifluoromethylphenyl, Benzyl, Fluorenyl, Carbazolyl, Cyclohexyl, Menthyl, Allyl, Hydroxyphenyl, Pentafluorophenyl, Carboxyphenyl, Naphthyl, Pyridyl, Furyl, Bis-(trifluoromethyl)-phenyl, Carbene, N-heterocyclic Carbene, Imidazolyl, Pyridazinyl, Pyrazinyl, Pyrimidyl, Phosphinyl, any aromatic rings fused with the central N-containing esatomic ring, such as

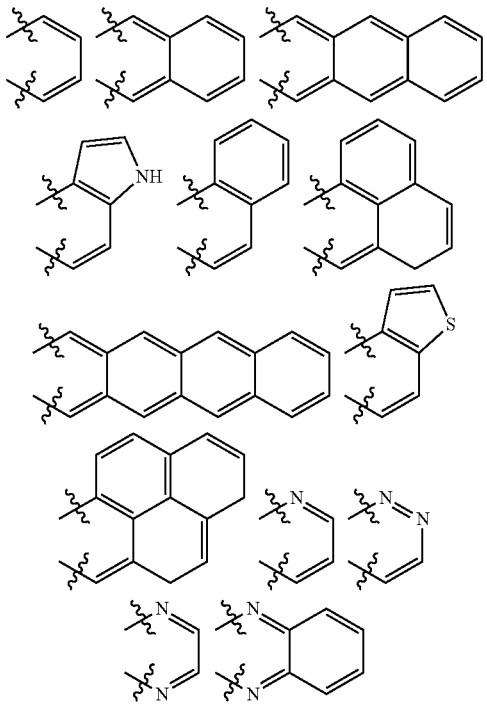

and wherein $X_1, X_2, X_3, X_7, X_8, X_9, X_{10}, X_{11}, X_{12}, X_{13}, X_{14}, X_{15}, X_{16}, X_{17}$ and $X_{18}$ are carbon and nitrogen atoms, that independently combine in such a way to have heterocycles selected from the group comprising pyrroles, diazoles, triazoles, tetrazoles, and wherein $R_{4-9}$, $R_{22-27}$ or $R_{31-36}$ are selected from the group of mono- or polyatomic substituents,
and wherein the platinum ion is coordinated to a ligand L and/or L' which is neutral, mono- or multi- either positively or negatively charged to yield a neutral-core complex, wherein the molecule is either fully neutral or either positively or negatively charged.

It is intended that L and/or L' comprise on remote sites —$SO_3^-$, —$OSO_3^-$, -phosphonium, —$COO^-$, alkylammonium, aminoacid, phosphate.

Further a platinum(II) complex is provided, wherein $X_1, X_2, X_3, X_7, X_8, X_9, X_{10}, X_{11}, X_{12}, X_{13}, X_{14}, X_{15}, X_{16}, X_{17}$ and $X_{18}$ represent independently from each other a carbon atom and $R_{4-9}$, $R_{22-27}$ or $R_{31-36}$, respectively, are selected from the group comprising H, F, Cl, Br, I, $CH_3$, $CF_3$, $NO_2$, OH, tiocyanate, isotiocyanate, —NCO, —CN, CHO, COOH, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, linear or branched, chiral or achiral, from 2 till 18 carbon atom containing any combination of the following groups: $CF_3$, $NO_2$, OH, CHO, COOH, tiocyanate, isotiocyanate, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, aliphatic or alicyclic alkyl, alkenyl, alkynyl, aryl, ester, carboxy, amine, sulfoxide, amide, phosphine or neutral heterocyclic moieties such as ethyl, n-propyl, phosphine, n-Butyl, t-Butyl, iso-Propyl, Hexyl, $F(CF_2)_m(CH_2)_n$— (m=1-10, n=0-4), $F(CF_2)_m(CH_2)_nC_6H_4$— (m=1-10, n=0-4), $O(CH_2CH_2O)_nCH_3$ (n=0-10000), haloalkyl, mono- or, disulfide, natural or synthetic sugar residuals, biotin, phosphonium moiety, aminoacidic residual, antibody, Phenyl, Chlorophenyl, Tolyl, Anisyl, Trifluoromethylphenyl, Benzyl, Fluorenyl, Carbazolyl, Cyclohexyl, Menthyl, Allyl, Hydroxyphenyl, Pentafluorophenyl, Carboxyphenyl, Naphthyl, Pyridyl, Furyl, Bis-(trifluoromethyl)-phenyl, Carbene, N-heterocyclic Carbene, Imidazolyl, Pyridazinyl, Pyrazinyl, Pyrimidyl, Phosphinyl, any aromatic rings fused with the central N-containing esatomic ring, such as

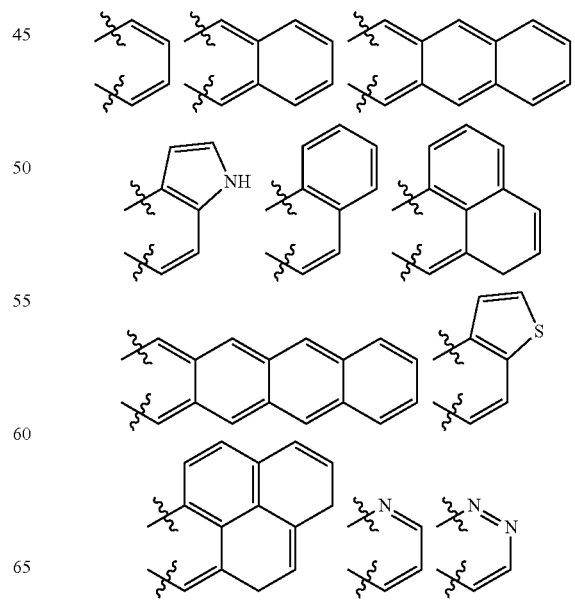

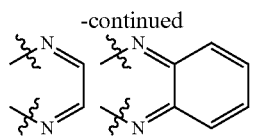

In a further embodiment the tridentate ligand of the platinum(II) complex is dianionic and L is a neutral monodentate ligand coordinating through nitrogen, phosphorus, carbon, sulphur, arsenic.

In a platinum(II) complex according to formula (I) L may coordinate through nitrogen and corresponds to formula (III) or (IV)

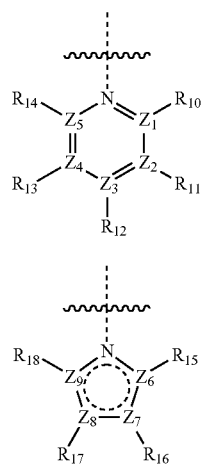

wherein $Z_1$, $Z_2$, $Z_3$, $Z_4$, $Z_5$, $Z_6$, $Z_7$, $Z_8$ and $Z_9$ represent independently carbon or nitrogen with the provisio
  if $Z_1$ is a nitrogen atom, then $R_{10}$ is absent;
  if $Z_2$ is a nitrogen atom, then $R_{11}$ is absent;
  if $Z_3$ is a nitrogen atom, then $R_{12}$ is absent;
  if $Z_4$ is a nitrogen atom, then $R_{13}$ is absent;
  if $Z_5$ is a nitrogen atom, then $R_{14}$ is absent;
  if $Z_6$ is a nitrogen atom, then $R_{15}$ is absent;
  if $Z_7$ is a nitrogen atom, then $R_{16}$ is absent;
  if $Z_8$ is a nitrogen atom, then $R_{17}$ is absent;
  if $Z_9$ is a nitrogen atom, then $R_{18}$ is absent;
wherein $R_{10}$, $R_{11}$, $R_{12}$, $R_{13}$, $R_{14}$, $R_{15}$, $R_{16}$, $R_{17}$ and $R_{18}$ are selected independently from the group comprising H, F, Cl, Br, I, $CH_3$, $CF_3$, $NO_2$, OH, tiocyanate, isotiocyanate, —NCO, —CN, CHO, COOH, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, linear or branched, chiral or achiral, from 1 till 18 carbon atom containing any combination of the following groups: $CF_3$, $NO_2$, OH, CHO, COOH, tiocyanate, isotiocyanate, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, aliphatic or alicyclic alkyl, alkenyl, alkynyl, aryl, ester, carboxy, amine, sulfoxide, amide, phosphine or neutral heterocyclic moieties such as ethyl, n-propyl, phosphine, n-Butyl, t-Butyl, iso-Propyl, Hexyl, $F(CF_2)_m(CH_2)_n$— (m=1-10, n=0-4), $F(CF_2)_m(CH_2)_nC_6H_4$— (m=1-10, n=0-4), $O(CH_2CH_2O)_nCH_3$ (n=0-10000), haloalkyl, mono- or, disulfide, natural or synthetic sugar residual, biotin, phosphonium moiety, aminoacidic residual, antibody, Phenyl, Chlorophenyl, Tolyl, Anisyl, Trifluoromethylphenyl, Benzyl, Fluorenyl, Carbazolyl, Cyclohexyl, Menthyl, Allyl, Hydroxyphenyl, Pentafluorophenyl, Carboxyphenyl, Naphthyl, Pyridyl, Furyl, Bis-(trifluoromethyl)-phenyl, Carbene, N-heterocyclic Carbene, Imidazolyl, Pyridazinyl, Pyrazinyl, Pyrimidyl, Phosphinyl, any aromatic rings fused with the central N-containing Pt-coordinating ring, such as

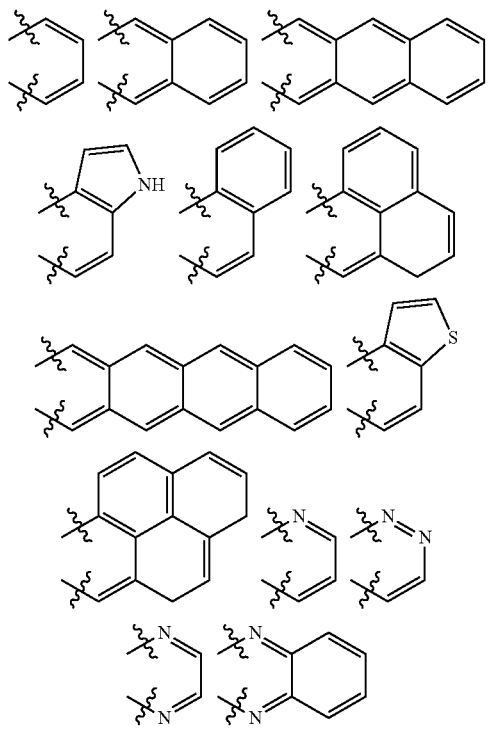

It is further intended that L may coordinate through phosphorus and L is $PAr_3$, $PR_3$, $P(OR)_3$ or L may coordinate through carbon, wherein L is a N-heterocyclic carbene, carbonyl, or L may coordinate through As, wherein L is $AsR_3$, $AsAr_3$ The tridentate ligand can be mono-anionic and L can be a mono-anionic ligand selected from the group comprising —Cl, —Br, —I, —CN, —NCS, —NSC, —NCO, —SR, —SAr, —OR, —OAr, pyrazolate, pyrrolate, carbazolate and azolates.

The tridentate ligand may also be dianionic and L may be a neutral monodentate ligand according to formula (II), coordinating through nitrogen, phosphorus or carbon, wherein the link between L and L' is selected from the group comprising

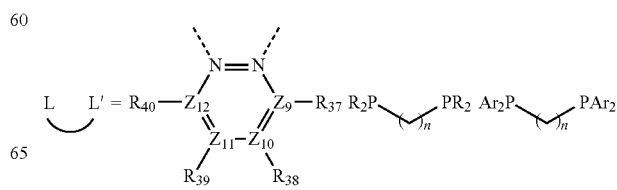

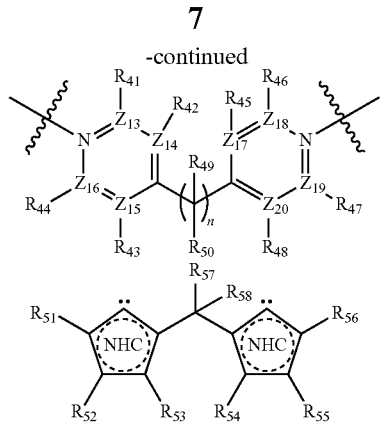

wherein $Z_{9-20}$ represent independently carbon or nitrogen with the proviso
- if $Z_9$ is a nitrogen atom, then $R_{37}$ is absent;
- if $Z_{10}$ is a nitrogen atom, then $R_{38}$ is absent;
- if $Z_{11}$ is a nitrogen atom, then $R_{39}$ is absent;
- if $Z_{12}$ is a nitrogen atom, then $R_{40}$ is absent;
- if $Z_{13}$ is a nitrogen atom, then $R_{41}$ is absent;
- if $Z_{14}$ is a nitrogen atom, then $R_{42}$ is absent;
- if $Z_{15}$ is a nitrogen atom, then $R_{43}$ is absent;
- if $Z_{16}$ is a nitrogen atom, then $R_{44}$ is absent;
- if $Z_{17}$ is a nitrogen atom, then $R_{45}$ is absent;
- if $Z_{18}$ is a nitrogen atom, then $R_{46}$ is absent;
- if $Z_{19}$ is a nitrogen atom, then $R_{42}$ is absent;
- if $Z_{20}$ is a nitrogen atom, then $R_{48}$ is absent;

wherein $R_{41-58}$ are selected independently from the group comprising H, F, Cl, Br, I, $CH_3$, $CF_3$, $NO_2$, OH, tiocyanate, isotiocyanate, —NCO, —CN, CHO, COOH, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, linear or branched, chiral or achiral, from 1 till 18 carbon atom containing any combination of the following groups: $CF_3$, $NO_2$, OH, CHO, COOH, tiocyanate, isotiocyanate, keto, amine, mono- or di-alkylamino, mono- or diarylamino, alkoxy, heteroaryloxy, alkoxycarbonil, acyloxy, acylamino, mercapto, sulfonylamino, cyano, carbamoyl, sulfonylamino, sulfamoyl, sulfinyl, aliphatic or alicyclic alkyl, alkenyl, alkynyl, aryl, ester, carboxy, amine, sulfoxide, amide, phosphine or neutral heterocyclic moieties such as ethyl, n-propyl, phosphine, n-Butyl, t-Butyl, iso-Propyl, Hexyl, $F(CF_2)_m(CH_2)_n$— (m=1-10, n=0-4), $F(CF_2)_m(CH_2)_nC_6H_4$— (m=1-10, n=0-4), $O(CH_2CH_2O)_nCH_3$ (n=0-10000), haloalkyl, mono- or, disulfide, natural or synthetic sugar residual, biotin, phosphonium moiety, aminoacidic residual, antibody, Phenyl, Chlorophenyl, Tolyl, Anisyl, Trifluoromethylphenyl, Benzyl, Fluorenyl, Carbazolyl, Cyclohexyl, Menthyl, Allyl, Hydroxyphenyl, Pentafluorophenyl, Carboxyphenyl, Naphthyl, Pyridyl, Furyl, Bis-(trifluoromethyl)-phenyl, Carbene, N-heterocyclic Carbene, Imidazolyl, Pyridazinyl, Pyrazinyl, Pyrimidyl, Phosphinyl, any aromatic rings fused with the central N-containing Pt-coordinating ring, such as

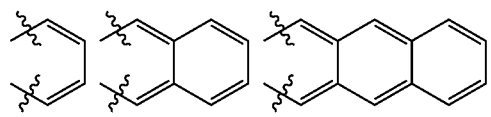

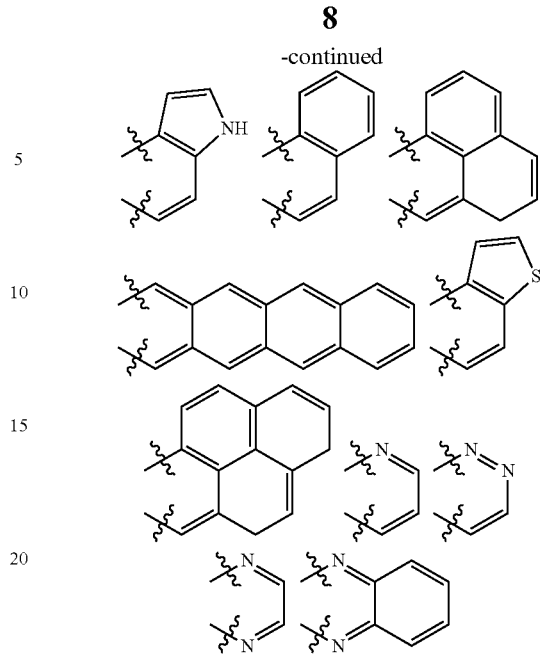

A platinum complex is provided, wherein the ligand can be covalently bound to biomolecules selected from the group comprising a polypeptide or protein, a nucleoside or a nucleotide chain and a sugar or sugar moiety.

The platinum(II) complex can also be in the aggregate form wherein the photophysical properties changes upon aggregation of the complex.

It is also envisaged that the platinum(II) complex is coupled to a targeting agent.

Another object of the invention is a use of a platinum(II) as imaging agent in vitro or in vivo. Further the platinum(II) complex can be used in therapeutic or diagnostic applications. In particular the loss of aggregation can be used to liberate toxic monomers in a detection method. The platinum (II) complex according to the invention is also intended for the detection of an analyte.

DETAILED DESCRIPTION OF THE FIGURES

Figure 1:
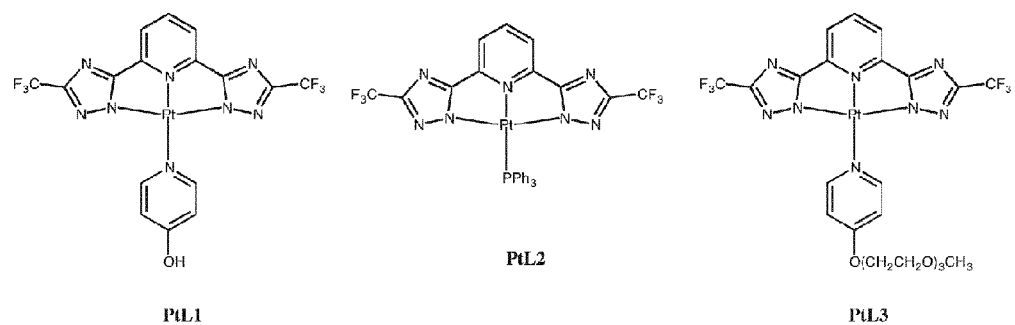
FIG. 1 Platinum(II) complexes: PtL1 capable of self-assembly in the nucleus, PtL2 unable to form aggregates and staining the cytoplasm, PtL3 analogous to PtL1 but completely soluble in water.

FIG. 1 shows examples of molecules according to the disclosure, which can be uptaken by cells. PtL1 is able to self-assemble within the nucleus, while PtL2 stains only the cytoplasm. Also PtL3, which is completely water-soluble enters into the nucleus and forms aggregates.

The examples demonstrate that the choice of ligands and substituents is critical for the respective application of the disclosed platinum(II) complexes.

Figure 2:
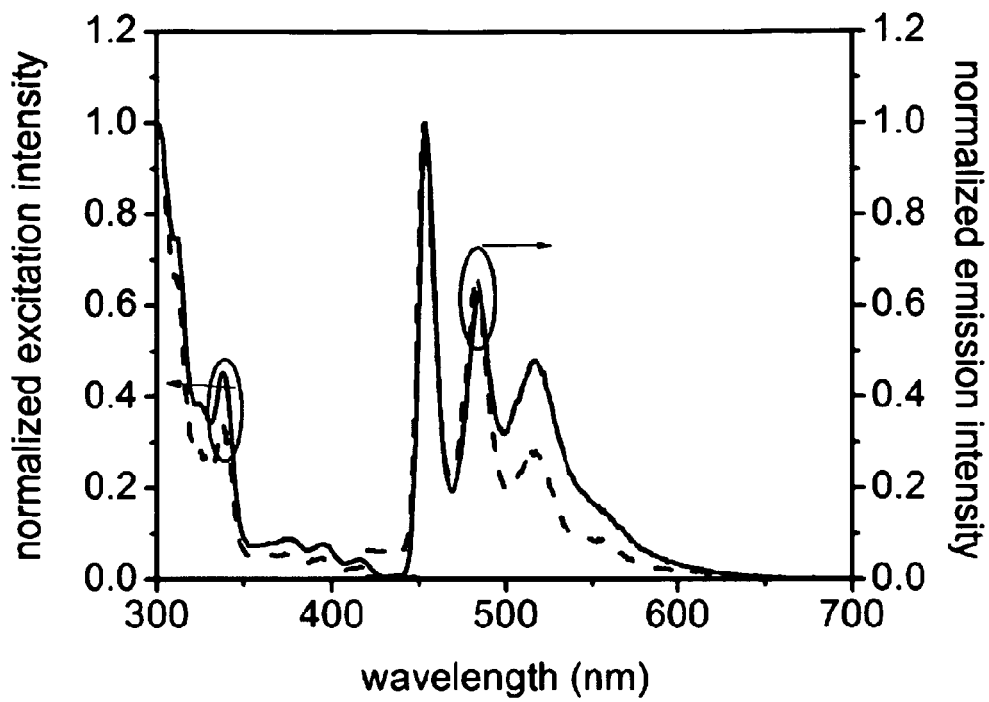
FIG. 2 Normalized excitation and emission spectra for monomeric PtL1 (upper) and its aggregated form (lower).
Figure 2:
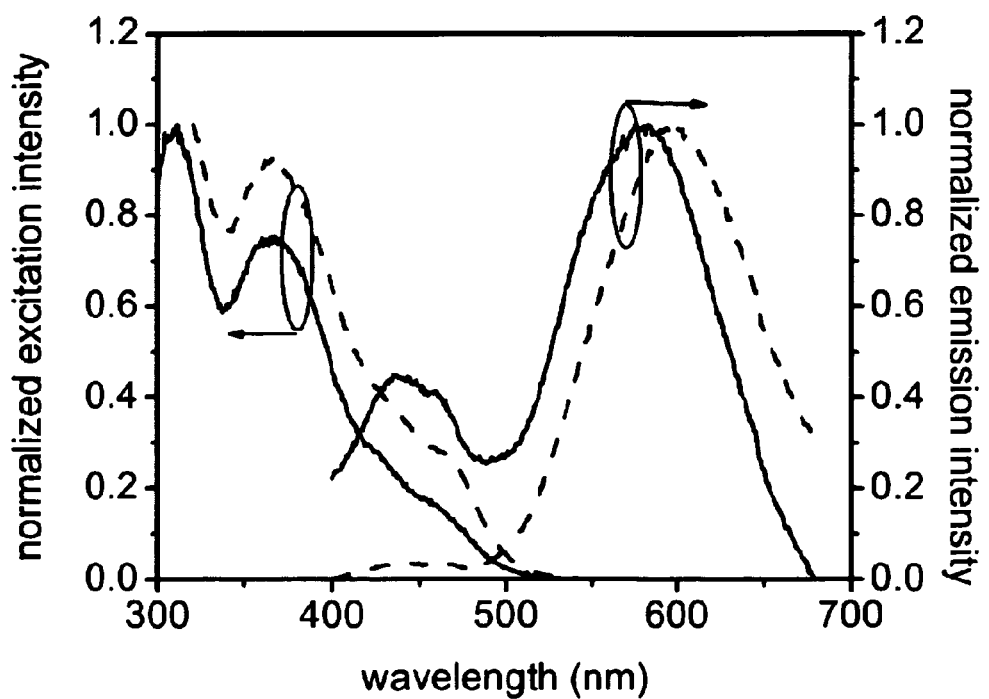

FIG. 2 shows normalized excitation and emission spectra in 2MeTHF at 77K for PtL1. Sample concentrations were $1.0 \times 10^{-4}$ M (solid line) and $1.0 \times 10^{-5}$ M (dotted line). The samples were excited at 300 nm (upper) and 350 (lower) for the emission spectra and for excitation the spectra were acquired at 580 nm.

The upper spectra show emission bands at 450 nm (upper) and the aggregated platinum complexes in cell culture medium. The emission quantum yields for a series of platinum complexes possessing the same tridentate is comparable and can be as high as 74%.

Figure 3:
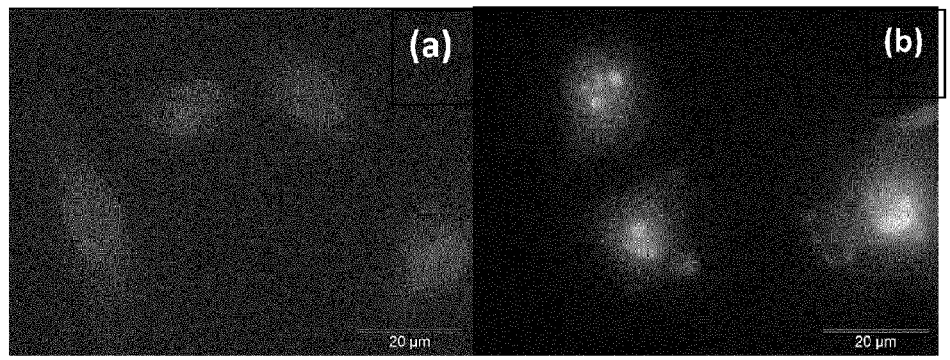
FIG. 3 Uptake of the complex PtL1 and its aggregates formation inside the nucleus after 2 hours incubation FIG. 4 Cell uptake kinetics of PtL1 at indicated time-points FIG. 5 Fluorescence microscopy images of cell uptake of PtL1 after 4 h incubation time FIG. 6 Emission spectra of platinum(II) complexes with different incubation times in the cell: a. 30 min, b. 4 h FIG. 7 Cell uptake PtL3

FIG. 3 shows the uptake of PtL1 and its aggregates formation inside the nucleus after 2 h incubation. FIG. 3 a shows excitation at 360-370 nm and FIG. 3 b shows excitation at 460-490 nm of PtL1.

Figure 4:
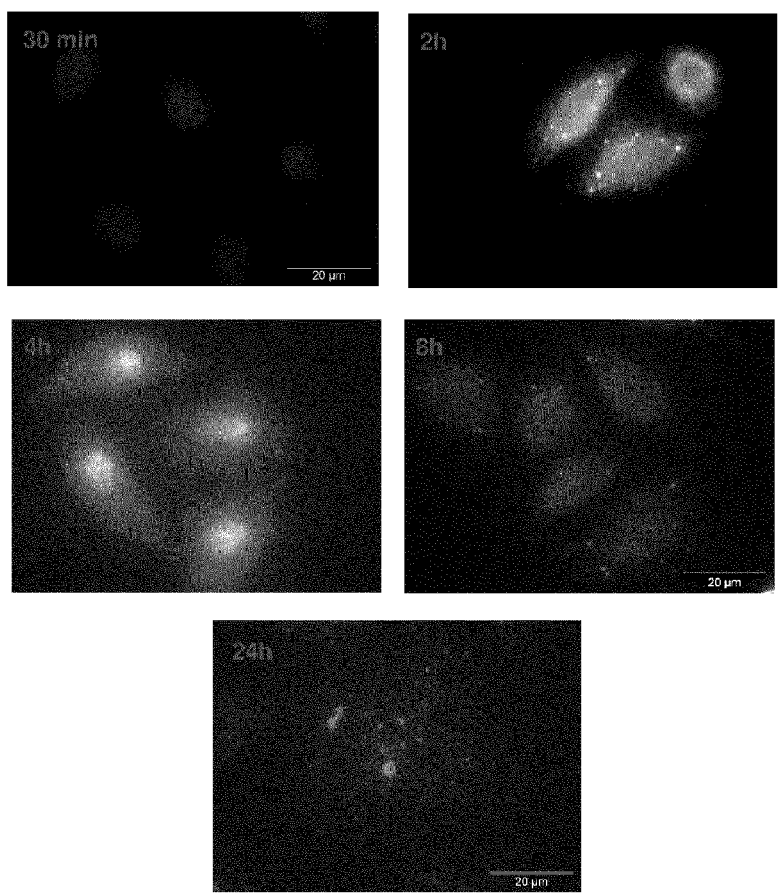

FIG. 4 shows uptake kinetic of PtL1 at the indicated incubation times. After 4 h a maximum uptake into the nucleus can be observed. Longer incubation times result in a decrease of staining.

Figure 5:
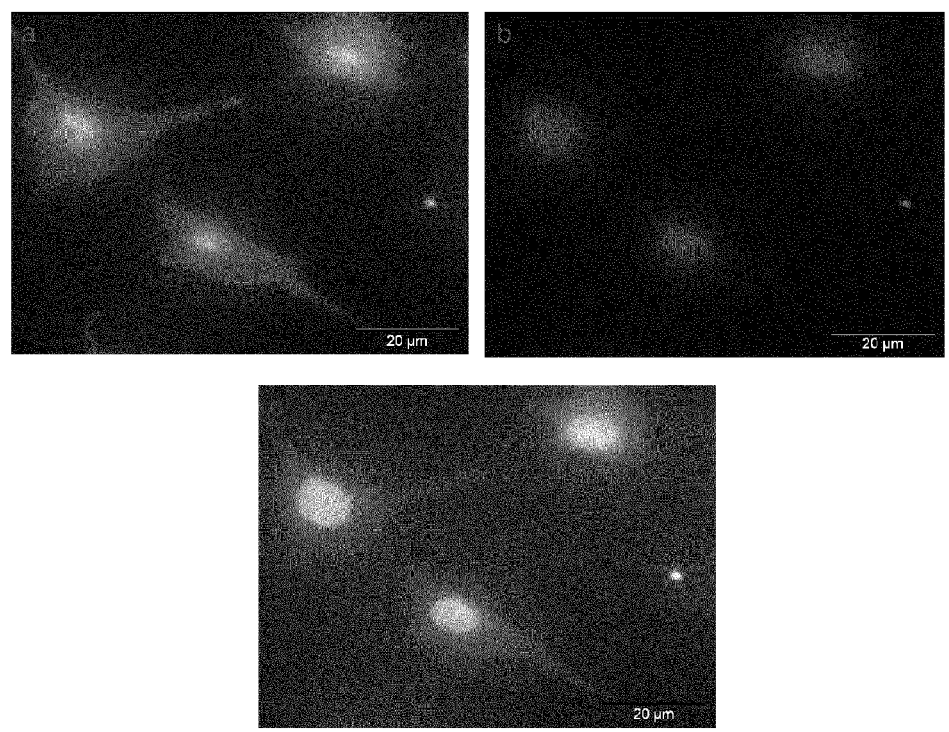

FIG. 5 shows in a) and b) excitation at different excitation ranges. In FIG. 5 a excitation at 360-370 nm is shown, while FIG. 5 b) shows excitation at 460-490 nm. FIG. 5c shows an overlay at both excitation ranges. The specific accumulation in the nucleus is clearly visible.

Figure 6:
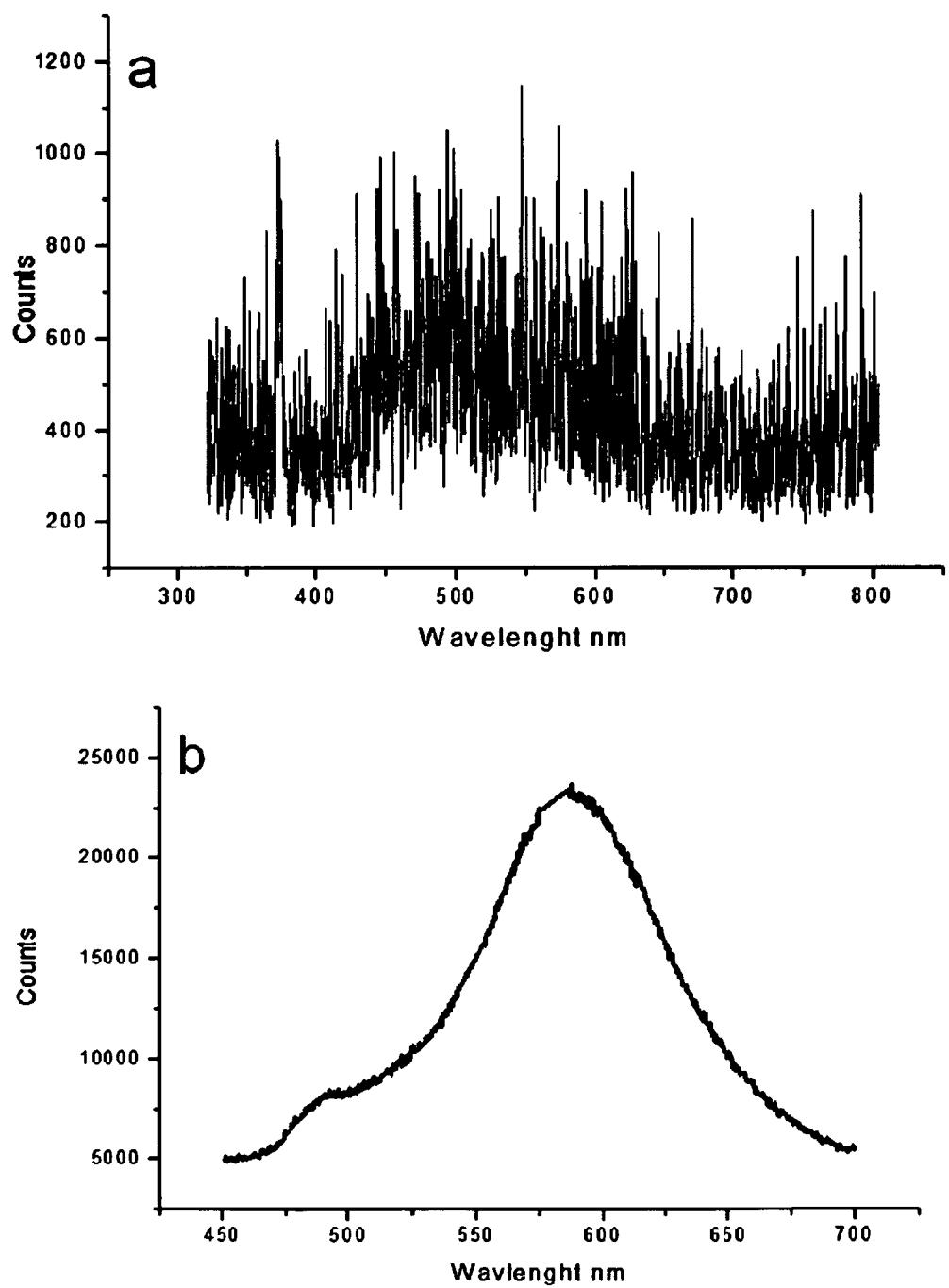

FIG. 6 shows emission spectra of the platinum complexes in cell. The monomeric platinum complex displayed after 30 minutes incubation in the cells very weak emission (a), while the aggregates of the platinum complex show a very intense emission after 4 h of incubation emission around $\lambda em=580$ nm as depicted in FIG. 6 b.

Figure 7:
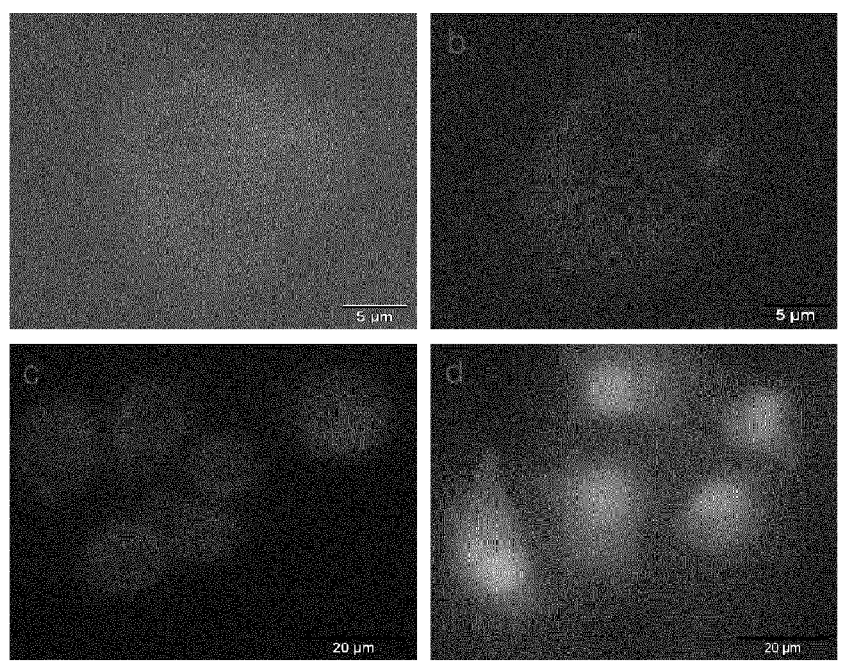

FIG. 7 shows the cell uptake of the water-soluble platinum complex PtL3. The increased water solubility results in a longer time until the complex is accumulated in the nucleus. After 30 minutes (a) or 2 h (b) no staining of nuclei is visible. Weak fluorescence is visible after 4 h incubation (c) and after 8 h (d) the nuclei are clearly and specifically stained.

Figure 8:
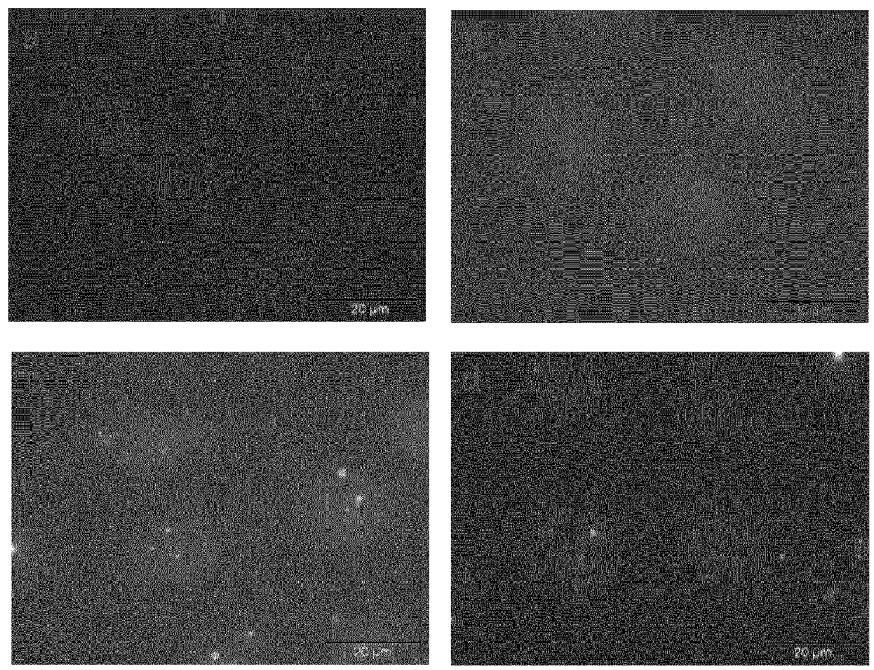
FIG. 8 Cell uptake PtL2

The same experimental setup was performed using complex PtL2. The results are shown in FIG. 8 and the time points correspond to FIG. 7. Obviously PtL2 enters the cells, but fails to aggregate in the nucleus. Due to the bulky phosphine ligand the complex seems not to be able to enter the nucleus so that no orange emission was detected. The compound stains only the cytoplasm.

Figure 9:
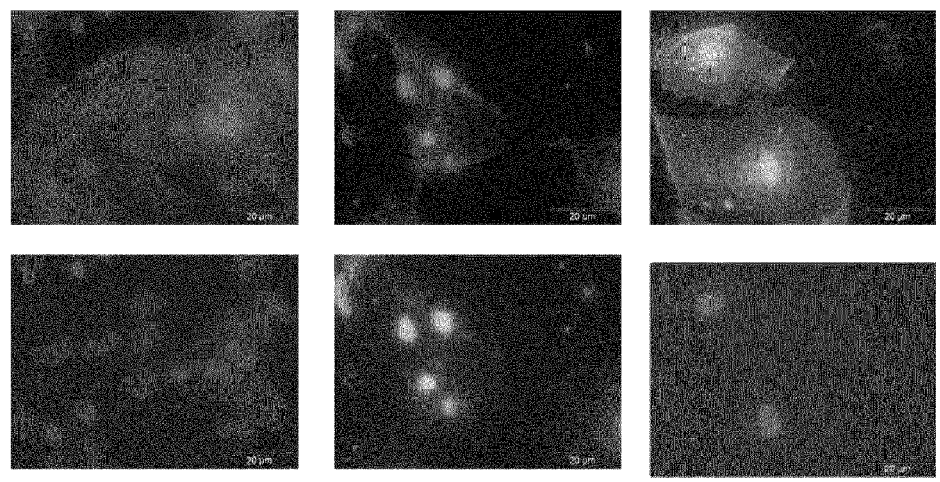
FIG. 9 Endothelial cell uptake kinetics of PtL1

FIG. 9 shows endothelial cell uptake kinetics of PtL1. FIG. 9 a, b show 30 min incubation, FIG. 9 c, d 2 h incubation and FIG. 9 e, f 4 h of incubation. The upper row shows fluorescence of PtL1, whereas the lower row shows DAPI-staining of the nuclei.

Figure 10:
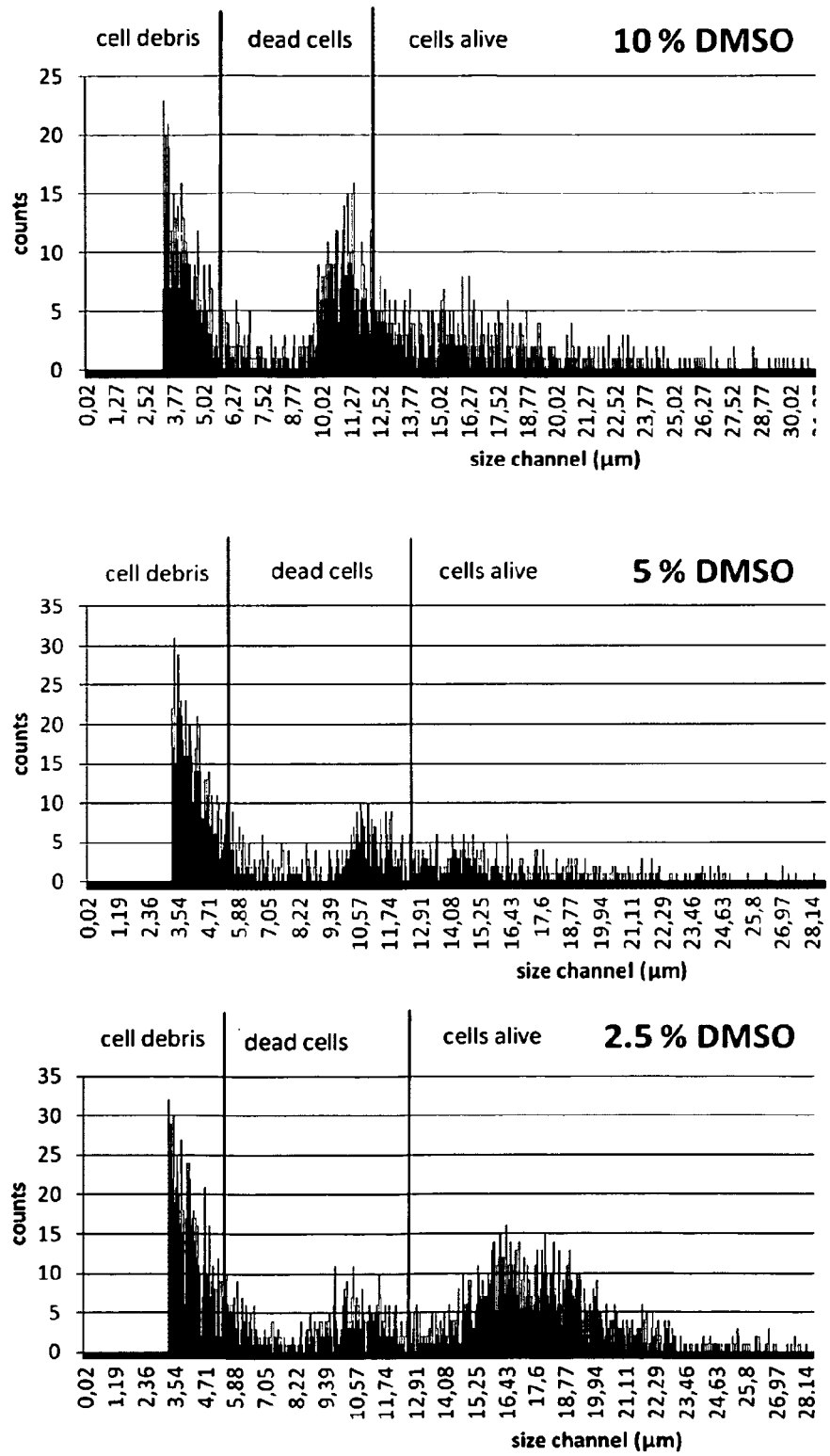
FIG. 10 Cytotoxicity results of different DMSO concentrations after 24 h incubation FIG. 11 Cell viability after incubation with complex PtL2 and PtL1
Figure 10:
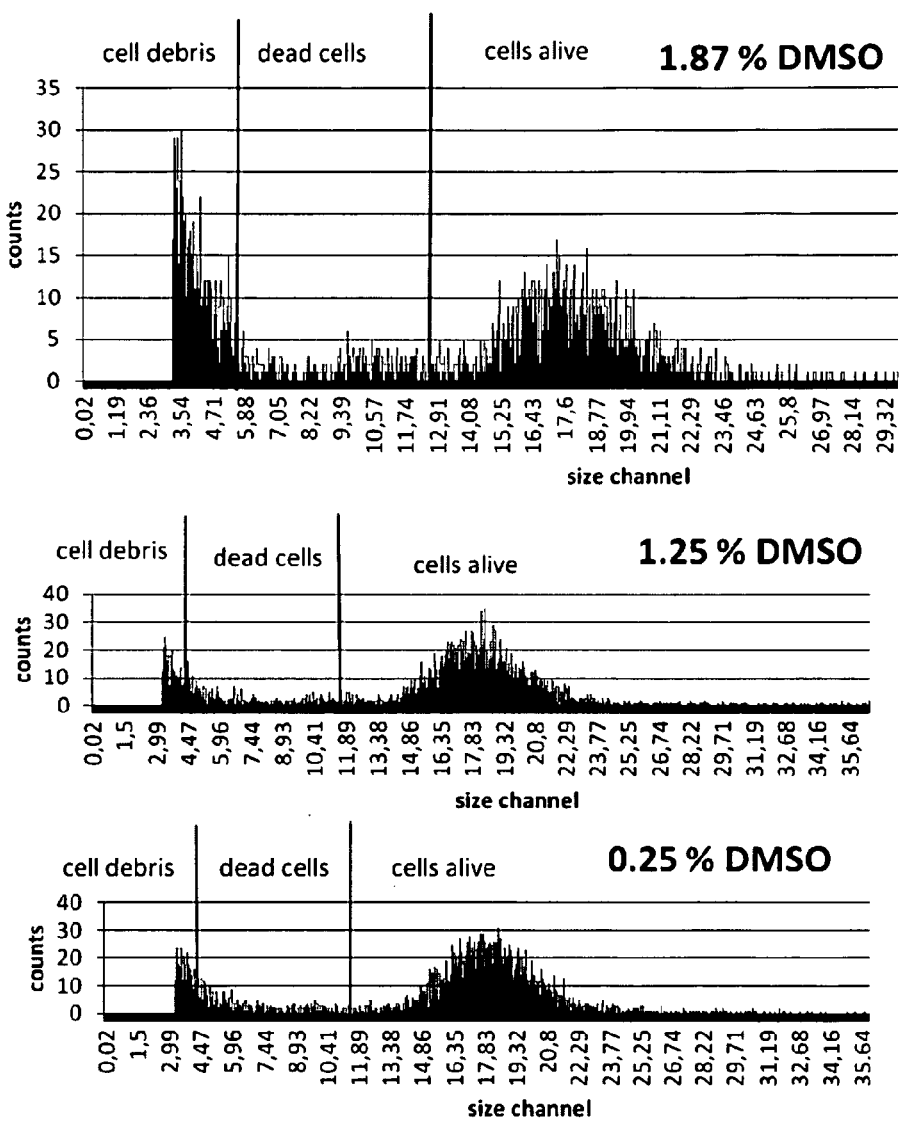

FIG. 10 shows cytotoxicity results of different DMSO concentrations after 24 h incubation. The used complex PtL1 was solved in DMSO and to exclude a toxic effect by DMSO in Hela-S3 cells viability studies were investigated by using a Casy-1 device. Different concentrations had to be checked in case of cytotoxicity and especially the best concentration of DMSO for ongoing experiments had to be determined The cytotoxicity experiments showed clearly that a DMSO concentration from 10% down to 5% is extremely toxic for the cells. Nearly no viable cells could be detected. A concentration of 2.5% DMSO showed already a high amount of viable Hela-S3 cells but still some dead cells were detected. Below 1.8% DMSO no toxic effect was detectable for Hela-S3 cells after 24 h incubation. For safety reasons in case of cytotoxicity the following experiments were performed at a concentration of 1% DMSO.

Figure 11:
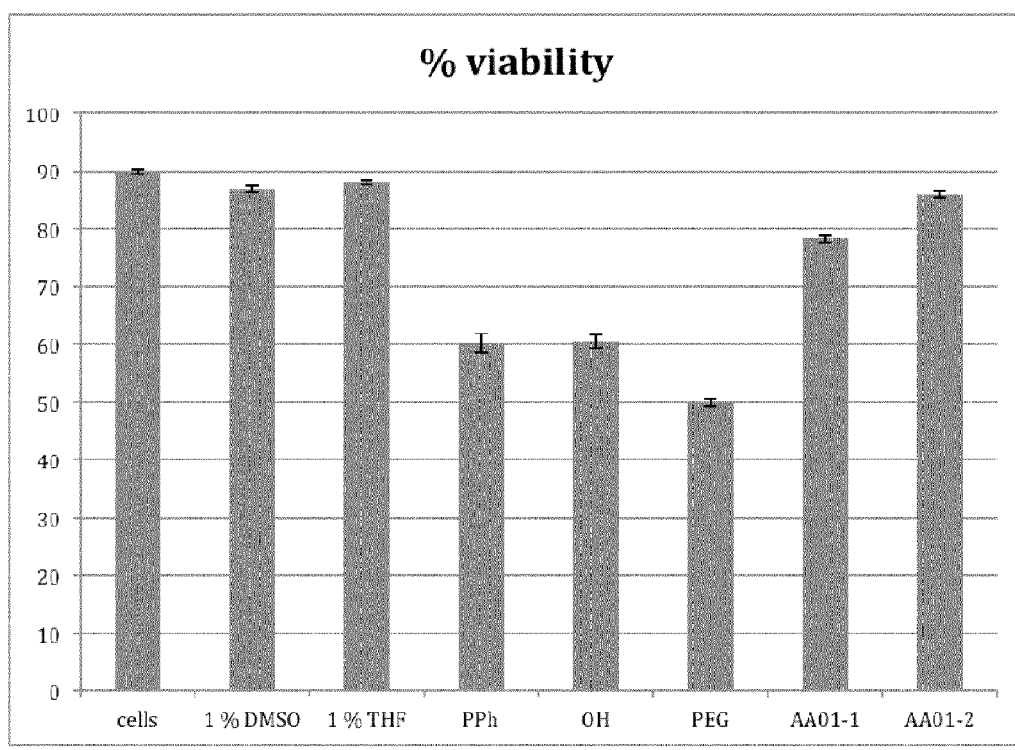

FIG. 11 shows cell viability after 24 h incubation with complex PtL1 (OH), PtL2 (PPH) and PTL3 (PEG). The performed experiments highlighted clearly that the incubation with complex PtL1 reduced the cell viability only about 26%. This gives us a serious consideration that this complex did not induce rapid cell death after 24 h. Additional experiments with complex PtL2 showed after a 24 h incubation a decreased viability of around 28% (see FIG. 11).

Figure 12:
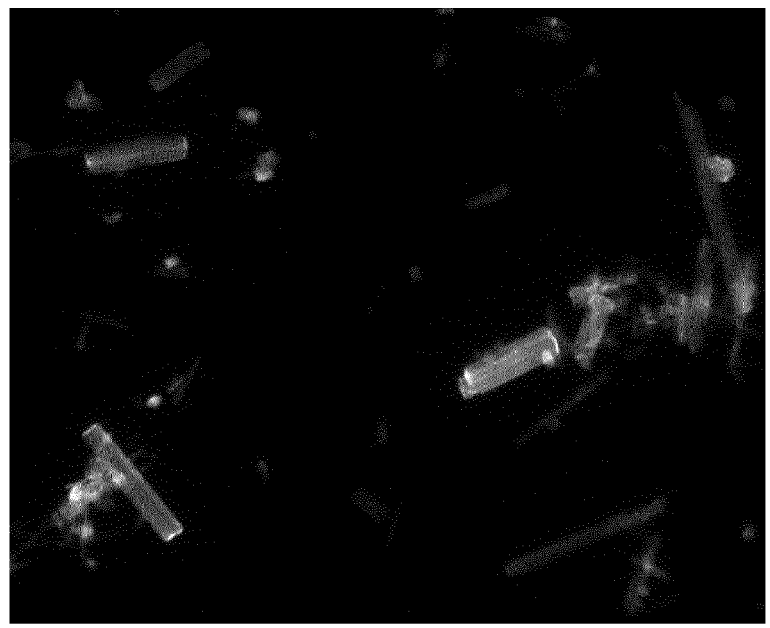
FIG. 12 Aggregate formation for PtL1

FIG. 12 shows an epifluorescence image of the aggregates formed in acetone of the PtL1.

Figure 13:
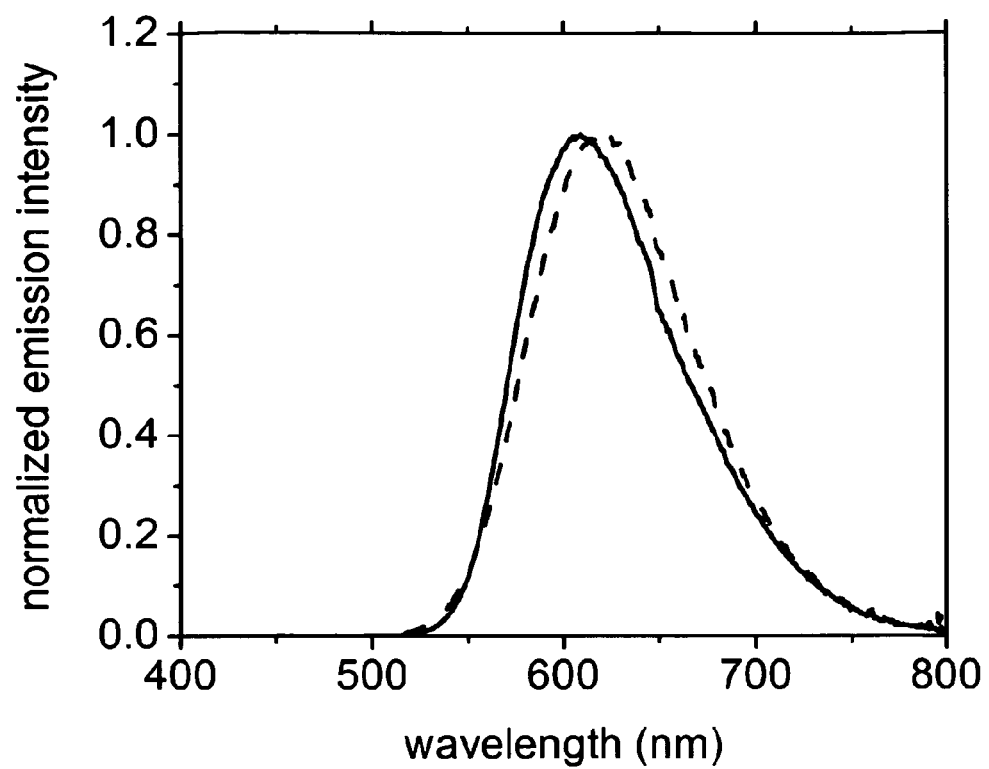
FIG. 13 Red emission of aggregate complexes

FIG. 13 shows the red emission of dinuclear compounds 12 and 13, when they are aggregated.

DETAILED DESCRIPTION OF THE INVENTION

This invention deals with the use of metal complexes and in particular, Pt ions coordinated to tridentate ligands coordinated via N—N—N. To fill the coordination sphere a fourth ligand is coordinated which could be e.g. pyridine, pyrazine, diazine, azoles, carbenes, phosphine, thiocyano, carboxylate, thiol, (di)sulfide, isotiocyanate, cyanate, carbonyl, halogens.

The invention focuses on the materials and on the emission properties of the metal complexes as well as the change in the emission properties, colour, excited state lifetimes, emission quantum yields, reactivity—including toxicity—, upon aggregation/disaggregation of the Pt complexes.

The aggregation can be independently controlled either with the tridentate ligand or with the ancillary ligand. Furthermore functionalization of one or more of the ligands leads to the localization of the Pt complexes in a desired part of the cell. The assembly to form aggregates is caused by the tendency of the platinum complexes to interact via the $dz^2$ orbitals and can be modulated by the ligands coordinated to the Pt ion. The assembly can be induced by the solvent, the interaction with biomolecules or by the template effect of DNA or RNA.

The general formulas of the complexes investigated are shown below where their synthesis is reported. The compounds are taken up by different type of cells and they are at the beginning localized in the cytoplasm as mononuclear species. Migration of the complexes in different part of the cell determines an increase of the local concentration of the Pt compounds leading to aggregates, if the case, which possess different photophysical and/or cytotoxicity properties.

Thus, the disclosed platinum complexes represent dynamic labels, because the monomeric species in the cytoplasm show e.g. blue emission, while the aggregates in the nucleus show orange emission due to the aggregated form. It is not only completely surprising that the complexes are able to stain the nucleus without being toxic, but also that the color depends on the cellular localization of the complexes.

It was demonstrated that imaging of the cytoplasm, and even more interesting of the nucleus, can occur (FIGS. 3, 4, 5, 7, 8, 9). The complexes can be hydrophilic or hydrophobic (on the metal moiety). In this last case the Pt units stay in the interior part of the aggregate, which can self-assemble in water or in the cell. Such localization determines a lack of sensitivity towards oxygen and possible quenchers in solution. Furthermore, their interaction with DNA, RNA or other vital parts of the cell is inhibited and therefore their toxicity is switched off. Imaging of portion or of the entire cell is possible and the brightness of the complexes is better than any existing molecular probe so far used for the imaging e.g. of the nucleus.

The present invention discloses new materials and their use as imaging agent. The formation of luminescent aggregates (see FIG. 12) can allow an enhancement or a change in colour of the emission leading to a dynamic label and on the formation of soft assemblies, which, in some cases, are even more emissive than the isolated corresponding species. The disclosed complexes (see e.g. FIG. 1) are suitable for uptake by cells, and their internalization. In particular a platinum complex with a similar structure to those used for tumor therapy is able to be uptaken as monomeric species, emitting blue light, by the cell and selectively accumulate into the nucleus. The complexes can accumulate in the e.g. nucleus of cancer cells (FIGS. 3, 4, 5, 7) or other type (e.g. epithelial or endothelial, FIG. 9) of cells and form luminescent aggregates. The process can be followed by simple epifluorescence microscopy since the platinum complex as monomeric species is a blue emitter and the aggregates are orange.

Organometallic complexes capable of self-assembly in cells in vivo have not been disclosed previously and it is the first time that any aggregate forms specifically inside the nucleus. Furthermore the formation of the aggregate leads to a turn off of the toxicity of the platinum complexes, which in principle should exert its toxicity upon intercalation into the DNA.

Toxicity studies showed on the other hand that the toxicity is very minor even after 48 hours of incubation.

Toxicity studies show that the toxicity can be modulated using different ligands (see FIG. 11)

The disclosed platinum(II) complexes provide several advantages:
- The complexes are suitable as dynamic labels for cells and can stain different part of the cell. In particular nucleus staining with visible emitters and long excited state lifetimes has been demonstrated. There are only very few nucleus dyes and they are all very toxic and short live.
- The colour of the emission of the aggregate is very suitable for microscopy and in vivo studies and many other colors can be developed with simple modification of the ligand. This allows having a completely new family of dyes for cell staining, covering the spectrum from ultraviolet to near-infrared (NIR).
- NIR Pt emitters either as monomers or aggregates can be used for in vivo imaging.
- The excited state lifetime of the emitter is extremely long compared with the existing dyes and therefore the measurements are easy and interference from biomolecules is avoided.
- The stability of the aggregate is very high and photo bleaching is less than for any other organic dye allowing longer observation time.
- By choosing appropriate tridentate and/or ancillary ligands it is possible to change solubility in organic solvents and/or water or modulate the degree of aggregation
- By choosing appropriate tridentate and/or ancillary ligands it is possible to influence the degree of aggregation, solubility in organic and/or aqueous solvents or to change the excited state properties and color of emission.
- Dinuclear or multinuclear complexes (FIG. 12) are used for the same purposes.

The disclosed complexes are intended for their use in in vitro and in vivo imaging. In vivo imaging comprises staining of living cells in cell culture or even the uptake of the platinum complexes via endovenous injection in animals.

EXPERIMENTAL PROCEDURES

Cell Uptake Kinetics with HeLa Cells: Approximately 50.000 HeLa cells (derived from cervical cancer) were seeded as a monolayer onto glass cover slips in a 6-well plate in Dulbecco's modified Eagle's medium Ham's F-12 supplement with 2% fetal bovine serum. The cells were incubated at 37° C. under a 5% $CO_2$ atmosphere for 24 h. After that the culture medium was removed and replaced with 2 ml medium containing the platinum complex (PtL1 or PtL2: 50 µM in 1% DMSO containing media or PtL3: 50 µM in 1% THF containing media) which was filtered with 0.2 µm membrane filter before used. After incubation at 37° C. or 4° C. for 30 min, 2 h, 4 h, 8 h, and 24 h the medium was removed, and the cell layer was washed gently with phosphate buffer solution (PBS, 1 mL×3) and fixed with 4% paraformaldehyde (PFA) solution for 10 min. Subsequently, cell layer was washed with PBS×2 and with water×3. Finally the cover slips were mounted onto glass slides for measurements. Observations were performed using a fluorescence microscopy (Microtime 200—PicoQuant GmbH, Germany) with a 100× oil immersion objective (Planapochromat, NA 1.4). The samples were excited with a 375 nm laser 40 kHz for lifetime measurements and for spectral measurements. The spectra were recorded on the same setup using a fibre-coupled spectrometer (Shamrock 163, Andor) and a back-illuminated CCD camera (Newton DU970N).

Endothelial Cell Uptake Kinetics: Approximately 50.000 endothelial cells were seeded as a monolayer onto gelatine coated glass cover slips in a 6-well plate in Dulbecco's modified Eagle's medium with 2% fetal bovine serum. The cells were incubated at 37° C. under a 5% $CO_2$ atmosphere for 24 h. After that the culture medium was removed and replaced with 2 ml medium containing the platinum complex PtL1, (50 µM in 1% DMSO containing media) which was filtered with 0.2 µm membrane filter before used. After incubation at 37° C. for 30 min, 2 h, and 4 h the medium was removed, and the cell layer was washed gently with phosphate buffer solution (PBS, 1 mL×3) and fixed with 4% paraformaldehyde (PFA) solution for 10 min. Subsequently, cell layer was washed with PBS×2 and with water×3. Finally, the fixed cell nucleus was stained with 4',6-diamidino-2-phenylindole (DAPI). The images were recorded with epifluorescence microscopy to follow the kinetics of uptake and formation of the Pt complex aggregates inside the cells.

Cytotoxicity Experiments: HeLa S3 cells were seeded into 12-well tissue culture dishes in a density of approximately 80000 cells per well. The logarithmically growing cells were cultured for 24 h in Ham's F12 nutrient mixture containing 10% fetal bovine serum, 100 U penicillin per mL and 100 mg streptomycin per mL and incubated at 37° C. with 5% CO2 in air and 100% humidity until the Pt-complexes were added. The cytotoxicity of the Pt-complexes was elucidated by quantifying the percentage of viable cells. Cell viability was measured after 24 h Pt-complex incubation and trypsinizing of cells, by an automatic cell counter (Casy-1, Roche Innovatis AG). These measurements are based on non-invasive (dye-free) electrical current exclusion with signal evaluation via pulse area analysis and allow the structural integrity of cells (membrane integrity and cell death).

Co-staining experiments: After incubation for 30 min, 2 h, 4 h, 8 h, and 24 h the medium was removed, and the cell layer was washed gently with phosphate buffer solution (PBS, 1 mL×3) and cell membrane was stained with red-fluorescent FM® 4-64 dyes (5 µg/ml in ice cold Hanks' balanced salt solution (HBSS) without magnesium or calcium) for 1 min. Then cell layer was fixed with 4% paraformaldehyde (PFA) solution for 10 min in ice. Subsequently, cell layer was washed with HBSS×2 and with water×3 and cell nucleus was stained with 4',6-diamidino-2-phenylindole (DAPI). Finally the cover slips were mounted onto glass slides for measurements. Observations were performed using a confocal fluorescence microscopy (Leica).

The Lifetime and Emission Spectra of the Pt Complex (PtL1) in the Cell Nucleus: The lifetime and emission spectra of the Pt complex in the cell nucleus were recorded by using a confocal fluorescence microscopy with a 100× oil immersion objective. The samples were excited with a 375 nm laser 2.5 kHz for lifetime measurements and for spectral measurements. The spectra were recorded on the same setup using a fibre-coupled spectrometer and a back-illuminated CCD camera. The lifetime measurements showed that the monomeric Pt-complex has a short lifetime, on the contrary the aggregate Pt-complex in the cell nucleus has a long lifetime (Table 1). Similar result was also shown by the measurement of the same Pt-complex ($1.0*10^{-5}$ M) in cell culture media.

TABLE 1

The lifetime values of platinum complex PtL1 with different incubation times in cells 5a: $5 \times 10^{-5}$M for 30 min; 5b $5 \times 10^{-5}$M for 4 h

| sample | $\lambda$ex [nm] | Lifetime [ns] |
|---|---|---|
| 5$^a$ | 375 | 4.8 |
| 5$^b$ | 375 | 198 |

The spectral measurements were also in agreement with the emission spectra of the Pt-complex in cell culture media. The monomeric Pt-complex (after 30 min incubation period in the cells) showed very weak emission and the Pt-complex as aggregates (after 4 h incubation period in the cells) showed emission around $\lambda$em=580 nm (FIG. 6).

Synthesis. All the reactions were carried out under nitrogen atmosphere. All the solvents and reagents are used as received from Aldrich, Fluka, TCI and VWR without further purification. $K_2PtCl_4$ was purchased from Precious Metal Online. $PtCl_2(DMSO)_2$ was prepared by following already reported synthetic procedures (R. Romeo, L. M. Scolaro Inorg. Synth. 1998, 32, 153). Column chromatography was performed with silica gel 60 (particle size 63-200 µm, 230-400 mesh, Merk). High-resolution electron spray ionization mass spectrometry (HR-ESI-MS) was performed on a Bruker Daltonics (Bremen, Germany) MicroToF with loop injection. $^1$H—$^{19}$F and $^{31}$P-NMR were carried out on an ARX 300 from Bruker Analytische Messtechnik (Karlsruhe, Germany). All these facilities were available at the Department of Chemistry, University of Muenster, Germany.

Photophysics. Absorption spectra were measured on a Varian Cary 5000 double-beam UV-vis-NIR spectrometer and baseline corrected. Steady-state emission spectra were recorded on an Edimburgh FS920 spectrometer equipped with a 450 W xenon-arc lamp, excitation and emission monochromators (1.8 nm/mm dispersion, 1800 grooves/mm blazed at 500 nm), and a Hamamatsu R928 photomultiplier tube. Emission and excitation spectra were corrected for sourse intensity (lamp and grating) by standard correction curves. Time resolved measurements were performed using the multichannel scaling (MCS) single-photon-counting or time-correlated single-photon-counting (TCSPC) option on the Horiba Jobin-Yvone IBH FL-322 Fluorolog 3. A pulsed xenon lamp was used to excite the sample in the case of MCS setup, while a pulsed NanoLED at 402 nm in the case of TCSPC. The excitation sources were mounted directly on the sample chamber at 90° to a double-grating emission monochromator (2.1 nm/mm dispersion, 1200 grooves/mm) and collected by a TBX-4-X single-photon-counting detector. The photons collected at the detector are correlated by a time-to-amplitude converter (TAC) to the excitation pulse. Signals were collecter using an IBH Data Station Hub photon-counting module, and data analysis was performed using the commercially available DAS6 software (HORIBA Jobin-Yvon IBH). The quality of the fit was assessed by minimizing the reduced $\chi^2$ function and by visual inspection of the weighted residuals. All solvent used for spectroscopical characterization were spectrometric grade and purchased by VWR.

Synthesis of Compound 1

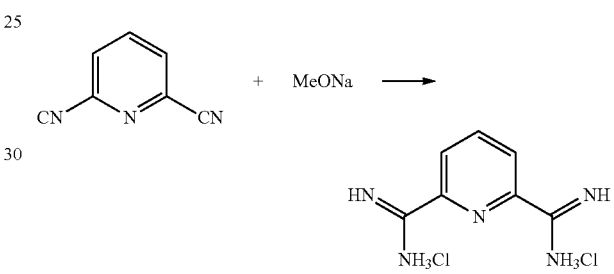

In a 500 mL round bottom flask 2,6-dicarbonitrile (20.0 g, 154.9 mmol, 1.0 eq.) and MeONa (1.67 g, 30.98 mmol, 0.2 eq) were dissolved in 180 mL of dry methanol. After refluxing for 6 h, ammonium chloride (12.8 g, 340.8 mmol, 2.2 eq.) was added to the reaction mixture and kept overnight under reflux. After cooling, the solid was filtered over a Buchner, washed with $Et_2O$, dried and collected as pure compound 1 (30.6 g, 130.2 mmol, yield 84.0%)

$^1$H NMR ($D_2O$, ppm) δ: 8.43 (1H, m)

HR-ESI-MS (positive scan): calcd. 235.04 uma. found 164.0903 [M-Cl—HCl]$^+$

Synthesis of Compound 2

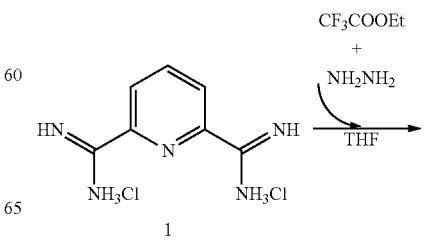

-continued

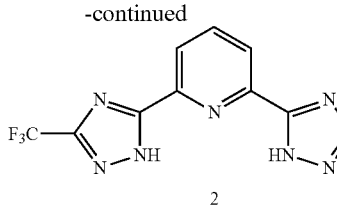

2

In a 500 mL round-bottom flask, ethyltrifluoroacetate (13.7 mL, 114.4 mmol, 2.2 eq.) was dissolved in 150 mL of THF and hydrazine monohydrate (6.15 mL, 126.7 mmol, 2.2 eq.) was added. The reaction mixture was refluxed for 2 h, then compound 1 (15.0 g, 63.5 mmol, 1 eq.) and sodium methoxide (2.54 g, 63.5 mmol, 1 eq.) were added. The reaction mixture was kept overnight refluxing under $N_2$. After cooling, the desired product (2) was purified from the crude on column chromatography by using silica gel as stationary phase and dichloromethane and acetone 9:1 as eluent (2.04 g, 5.84 mmol, yield 9.2%).

$^1$H NMR (CD$_2$Cl$_2$, ppm) δ: 13.82 (2H), 8.21 (2H), 8.06 (1H); $^{19}$F{$^1$H} NMR (CD$_2$Cl$_2$, ppm) δ: −65.61 (1F)

HR-ESI-MS (negative scan): calcd. 349.05 uma [M]; found 348.0457[M−H]$^-$

Synthesis of Compound 3, PtL2

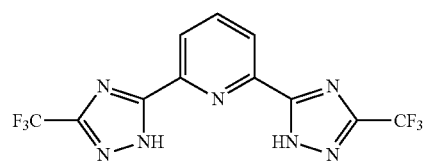

2

+ PtCl$_2$(DMSO)$_2$

+ PPh$_3$

→

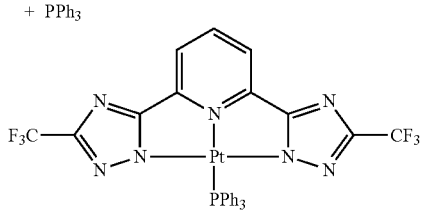

3

In a 250 mL round-bottom flask, compound 2 (1.40 g, 4.01 mmol, 1.1 eq.), PtCl$_2$(DMSO)$_2$ (1.54 g, 3.65 mmol, 1.0 eq.), triphenylphosphine (956 mg, 3.65 mmol, 1.0 eq.) were suspended in 130 mL of a 3:1 2-ethoxyethanol and water mixture. The reaction mixture was overnight heated at 85° C. Rapidly, a greenish-blue precipitate appeared. The desired compound (3), PtL2, was purified on column chromatography using as silica gel as stationary phase and 2:3 THF:n-hexane mixture as eluent and obtained as pale yellow solid (634 mg, 0.79 mmol, yield 22%).

$^1$H NMR (CD$_2$Cl$_2$, ppm) δ: 8.08 (1H), 7.83 (2H), 7.72-7.64 (6H), 7.51-7.44 (3H), 7.40-7.34 (6H); $^{19}$F{$^1$H} NMR (CD$_2$Cl$_2$, ppm) δ: −65.06 (1F); $^{31}$P{$^1$H} NMR (CD$_2$Cl$_2$, ppm) δ: 10.76 (1P)

HR-ESI-MS (positive scan): calcd. 804.09 uma [M]; found 805.0973 [M+H]$^+$; 827.0793 [M+Na]$^+$.

Synthesis of Compound 4

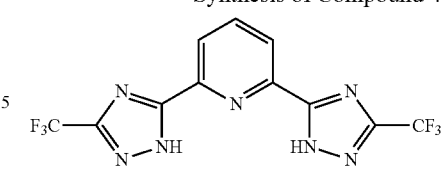

2

+ PtCl$_2$(DMSO)$_2$

+

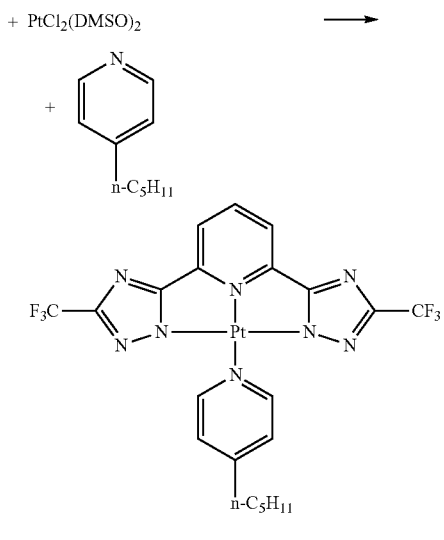

4

In a 50 mL round-bottom flask, compound 2 (280 mg, 0.80 mmol, 1.0 eq.), PtCl$_2$(DMSO)$_2$ (339 mg, 0.80 mmol, 1.0 eq.), 4-amylpyridine (145 μL, 0.80 mmol, 1.0 eq.) and triethylamine (100 μL) were suspended in 20 mL of a 3:1 2-ethoxyethanol and water mixture. The reaction mixture was overnight heated at 85° C. Rapidly, a yellowish-orange precipitate appeared. The desired compound (4) was purified on column chromatography using as silica gel as stationary phase and 1:1 THF:n-hexane mixture as eluent and obtained as yellowish-orange solid (166 mg, 0.24 mmol, yield 30.0%).

$^1$H NMR (CD$_2$Cl$_2$, ppm) δ: 9.36 (2H), 7.98 (1H), 7.72 (2H), 7.35 (2H), 2.69 (2H), 1.66 (2H), 0.87-0.72 (7H); $^{19}$F{$^1$H} NMR (CD$_2$Cl$_2$, ppm) δ: −64.81 (1F).

HR-ESI-MS (positive scan): calcd. 804.09 uma [M]; found 805.0973 [M+H]$^+$; 827.0793 [M+Na]$^+$.

Synthesis of Compound 5, PtL1

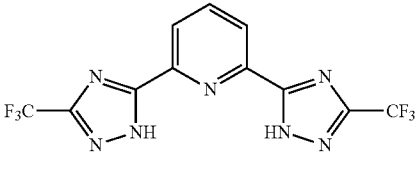

2

+ PtCl$_2$(DMSO)$_2$

+

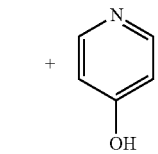

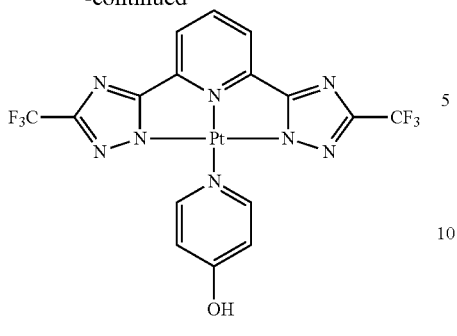

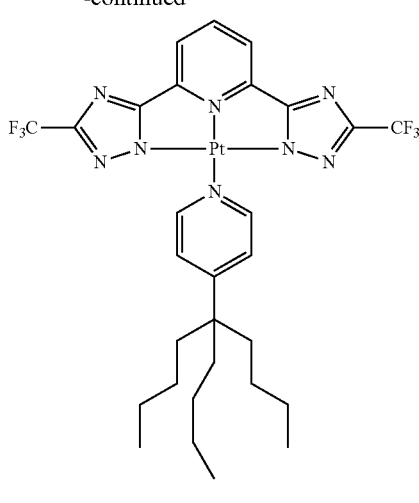

In a 50 mL round-bottom flask, compound 2 (230.0 mg, 0.660 mmol, 1.0 eq.), PtCl₂(DMSO)₂ (306.0 mg, 0.73 mmol, 1.1 eq.), 4-hydroxypyridine (63 µL, 0.660 mmol, 1.0 eq.) were suspended in 20 mL of a 3:1 2-ethoxyethanol and water mixture. The reaction mixture was overnight heated at 85° C. Rapidly, a yellowish-green precipitate appeared. The desired compound (5), PtL1 was purified on column chromatography using as silica gel as stationary phase and 3:1 THF:n-hexane mixture as eluent, and obtained as yellow solid (66.1 mg, 0.104 mmol, yield 15.7%).

$^1$H NMR (THF-d₈, ppm) δ: 9.31 (2H), 8.14 (1H), 8.72 (2H), 6.95 (2H); $^{19}$F{$^1$H} NMR (THF-d₈, ppm) δ: −65.10 (1F).

HR-ESI-MS (negative scan): calcd. 636.03246 uma [M]; found 636.03002 [M−H]⁻.

Synthesis of Compound 6

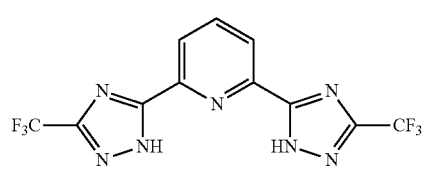

+ PtCl₂(DMSO)₂ ⟶

+

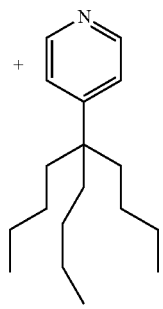

In a 100 mL round-bottom flask, compound 2 (335.0 mg, 0.96 mmol, 1.1 eq.), PtCl₂(DMSO)₂ (368.0 mg, 0.87 mmol, 1.0 eq.), 4-(1,1-dibutyl)pentylpyridine (200 µL, 0.87 mmol, 1.0 eq.) were suspended in 25 mL of a 3:1 2-ethoxyethanol and water mixture. The reaction mixture was overnight heated at 85° C. Rapidly, a plentiful green precipitate appeared. The desired compound (6) was purified on column chromatography using as silica gel as stationary phase and 1:2 THF:n-hexane mixture as eluent, and obtained as green solid (340.0 mg, 0.43 mmol, yield 44.0%).

$^1$H NMR (CD₂Cl₂, ppm) δ: 9.56 (2H), 8.03 (1H), 7.80 (2H), 7.52 (2H), 1.66 (6H), 1.21 (6H), 0.97 (6H), 0.80 (9H); $^{19}$F{$^1$H} NMR (CD₂Cl₂, ppm) δ: −64.58 (1F).

HR-ESI-MS (positive scan): calcd. 804.25330 uma [M+H]; found 804.25251 [M−H]⁺.

Synthesis of Compound 7

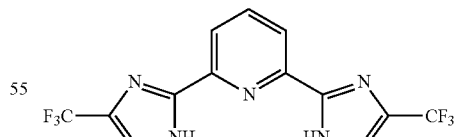

+ PtCl₂(DMSO)₂ ⟶

+ 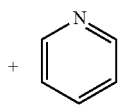

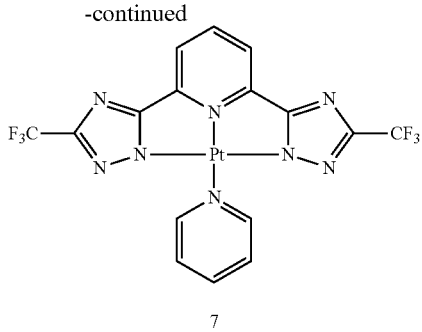

7

In a 100 mL round-bottom flask, compound 2 (381.8 mg, 1.09 mmol, 1.1 eq.), PtCl$_2$(DMSO)$_2$ (419.7 mg, 0.99 mmol, 1.0 eq.), and pyridine (80 μL, 0.99 mmol, 1.0 eq.) were suspended in 33 mL of a 3:1 mixture of 2-ethoxyethanol and water. The reaction mixture was overnight heated at 85° C. Rapidly, a plentiful greenish-yellow precipitate appeared. The desired compound (7) was purified on column chromatography using as silica gel as stationary phase and a gradient 1:1.5→2:1 of THF:n-hexane mixture as eluent, and obtained as green solid (383.0 mg, 0.617 mmol, yield 56.6%).

$^1$H NMR (CD$_2$Cl$_2$, ppm) δ: 9.61 (2H), 8.05 (2H), 7.80 (2H), 7.62 (2H); $^{19}$F{$^1$H} NMR (CD$_2$Cl$_2$, ppm) δ: −64.62.

HR-ESI-MS (positive scan): calcd. 621.04 uma [M+H]; found 622.04932 [M+H]$^+$.

Synthesis of Compound 8

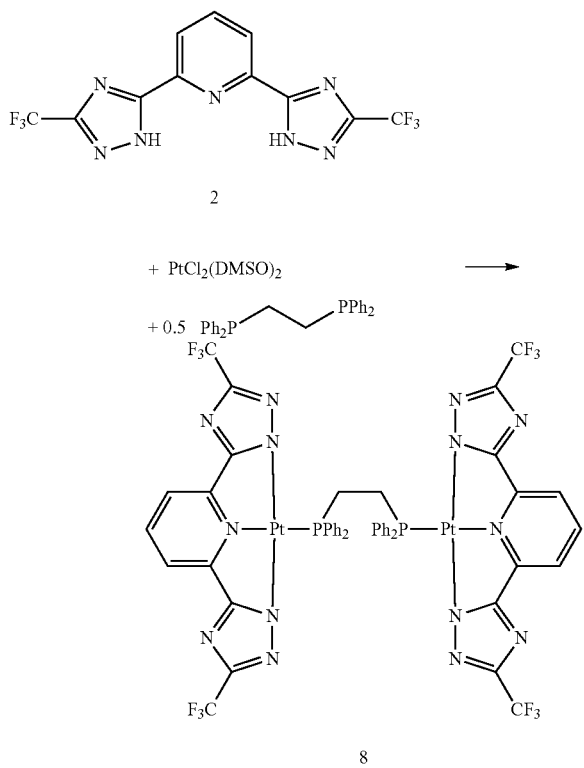

8

In a 100 mL round-bottom flask, compound 2 (197.8 mg, 0.57 mmol, 1.0 eq.), PtCl$_2$(DMSO)$_2$ (240.0 mg, 0.57 mmol, 1.0 eq.), bis-(diphenylphosphine)-ethane (113.1 mg, 0.28 mmol, 0.5 eq.) and triethylamine (198 μL, 2.5 eq.) were suspended in 16 mL of a 3:1 mixture of 2-ethoxyethanol and water. The reaction mixture was overnight heated at 85° C. Rapidly, the reaction mixture turned yellow and a plentiful pale yellow precipitate appeared. The desired compound (8) was purified on column chromatography using as silica gel as stationary phase and a gradient 2:1→1:1 of THF:n-hexane mixture as eluent, and obtained as pale yellow solid (124.0 mg, 0.08 mmol, yield 14.6%).

$^1$H NMR (CD$_2$Cl$_2$, ppm) δ: 8.11 (1H), 7.84 (2H), 7.63 (4H), 7.51 (2H), 7.35 (4H), 3.68 (2H); $^{19}$F{$^1$H} NMR (CD$_2$Cl$_2$, ppm) δ: −64.90 (1H), $^{31}$P{$^1$H} NMR (CD$_2$Cl$_2$, ppm) δ: 6.56 (1P).

HR-ESI-MS (positive scan): calcd. 1482.14 uma [M]; found 1505.1224 [M+Na]$^+$.

Synthesis of Compound 9

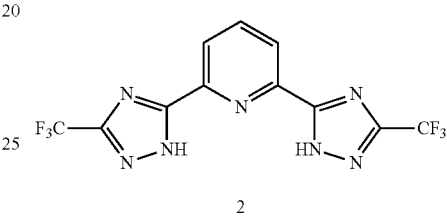

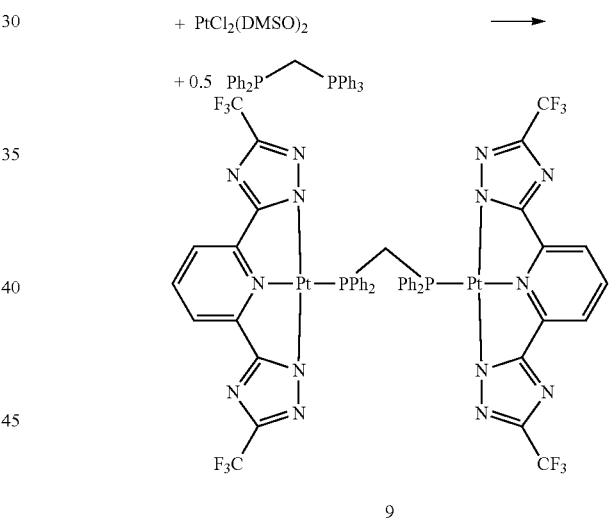

9

In a 100 mL round-bottom flask, compound 2 (264.0 mg, 0.76 mmol, 1.0 eq.), PtCl$_2$(DMSO)$_2$ (320.0 mg, 0.76 mmol, 1.0 eq.), bis-(diphenylphosphine)-methane (145.7 mg, 0.38 mmol, 0.5 eq.) and triethylamine (264 μL, 2.5 eq.) were suspended in 20 mL of a 3:1 mixture of 2-ethoxyethanol and water. The reaction mixture was overnight heated at 85° C. Rapidly, the reaction mixture turned yellow and a plentiful pale yellow precipitate appeared. The desired compound (9) was purified on column chromatography using as silica gel as stationary phase and a 1:1 THF:n-hexane mixture as eluent, and obtained as pale yellow solid (338.0 mg, 0.23 mmol, yield 30.2%).

$^1$H NMR (CD$_2$Cl$_2$, ppm) δ: 8.17 (1H), 7.86 (2H), 7.77 (4H), 7.21 (6H), 5.54 (1H); $^{19}$F{$^1$H} NMR (CD$_2$Cl$_2$, ppm) δ: −64.92 (1H), $^{31}$P{$^1$H} NMR (CD$_2$Cl$_2$, ppm) δ: −3.21 (1P).

HR-ESI-MS (positive scan): calcd. 1468.12 uma [M]; found 1469.12200 [M+H]$^+$.

Synthesis of Compound 10, PtL3

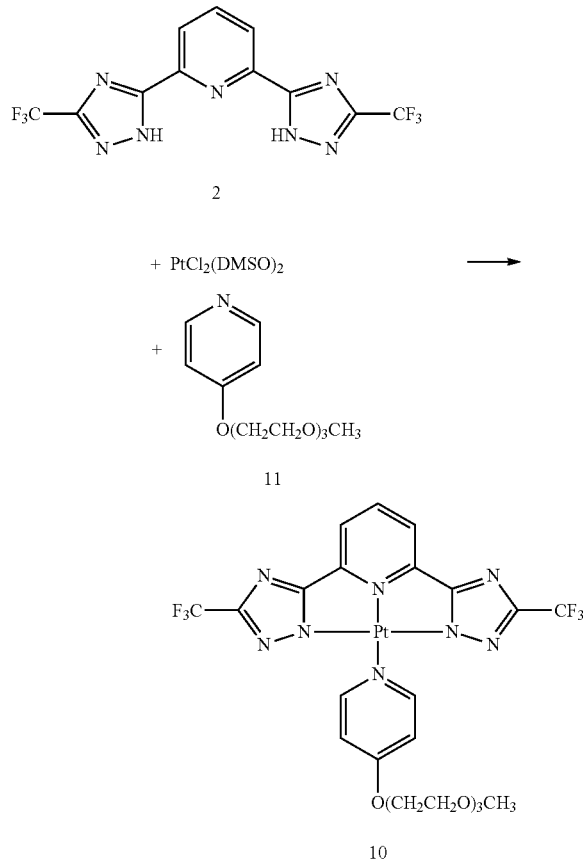

The compound 10, PtL3, was prepared accordingly to the same synthetic procedure used for the compounds 3-7, where the compound 11 was used as ancillary neutral ligand in order to increase the water-solubility of the final complex. The desired compound (9) was purified on column chromatography using as silica gel as stationary phase and acetone as eluent, and obtained as pale yellow solid (yield 76%).

Synthesis of Compound 12

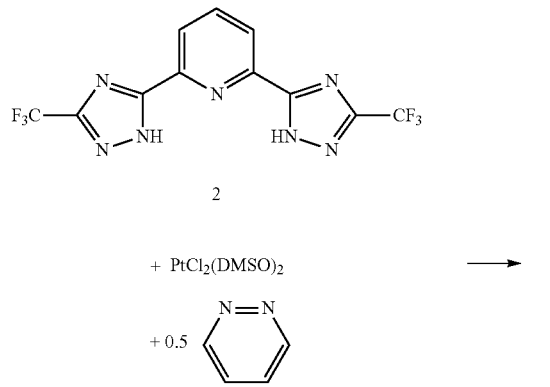

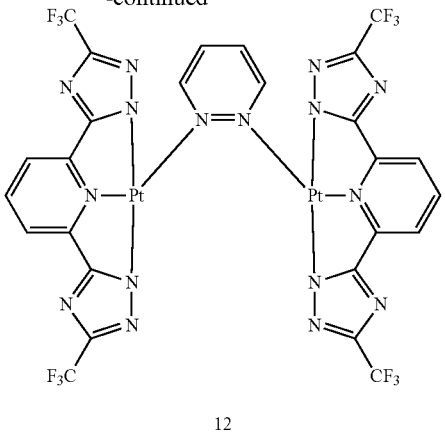

In a 100 mL round-bottom flask, compound 2 (1 eq.), PtCl$_2$(DMSO)$_2$ (1.0 eq.), pyridazine (0.5 eq.) and triethylamine (2.5 eq.) were suspended in 16 mL of a 3:1 mixture of 2-ethoxyethanol and water. The reaction mixture was overnight heated at 85° C. Rapidly, the reaction mixture turned yellow-orange and a plentiful orange precipitate appeared, corresponding to the desired compound 12 (yield 28%).

Synthesis of Compound 13

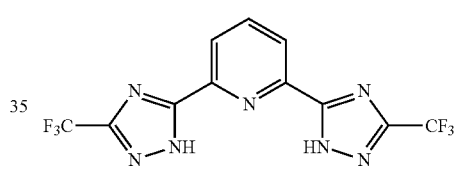

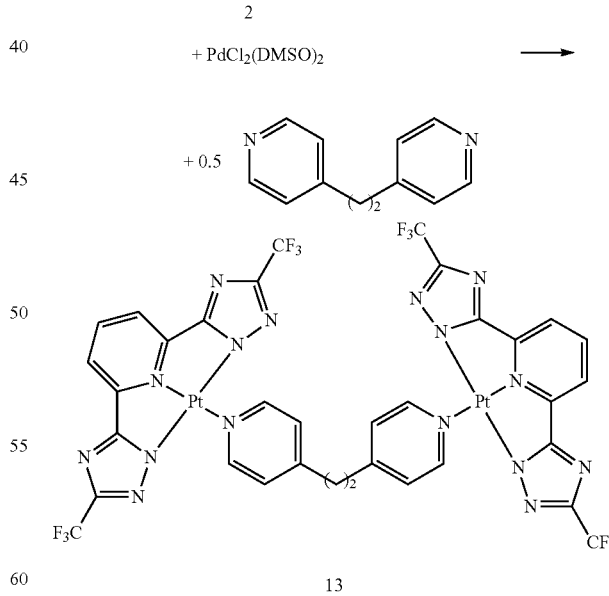

In a 100 mL round-bottom flask, compound 2 (1 eq.), PtCl$_2$(DMSO)$_2$ (1.0 eq.), 1,2-Bis(4-pyridyl)ethane (0.5 eq.) and triethylamine (2.5 eq.) were suspended in 16 mL of a 3:1 mixture of 2-ethoxyethanol and water. The reaction mixture was overnight heated at 85° C. Rapidly, the reaction mixture turned yellow-orange and a plentiful red precipitate appeared, corresponding to the desired compound 13.

The invention claimed is:
1. A process of using a platinum (II) complex according to one of formulas (I) or (II)

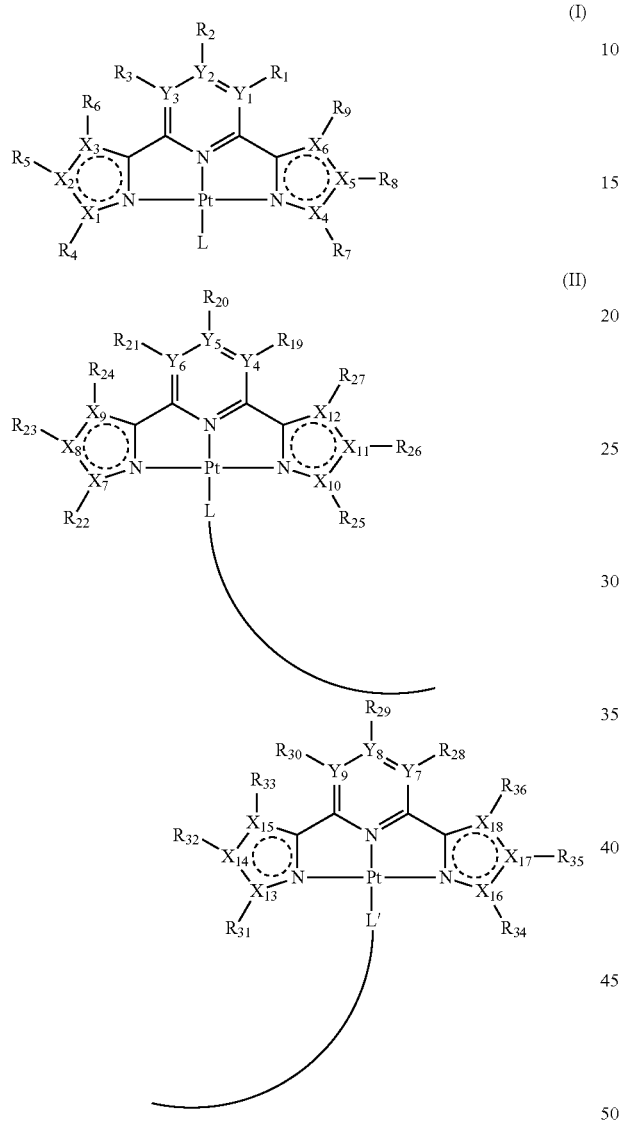

comprising a mono- or dinuclear N^N^N-type ligand
wherein $Y_1$, $Y_2$, $Y_3$, $Y_4$, $Y_5$, $Y_6$, $Y_7$, $Y_8$ and $Y_9$ can be independently either carbon or nitrogen with the proviso
if $Y_1$ or $Y_4$ are a nitrogen atom, then $R_1$ or $R_{19}$ are absent;
if $Y_2$ or $Y_5$ are a nitrogen atom, then $R_2$ or $R_{20}$ are absent;
if $Y_3$ or $Y_6$ are a nitrogen atom, then $R_3$ or $R_{21}$ are absent;
if $Y_7$ is a nitrogen atom, then $R_{28}$ is absent;
if $Y_8$ is a nitrogen atom, then $R_{29}$ is absent;
if $Y_9$ is a nitrogen atom, then $R_{30}$ is absent,
and if $Y_1$, $Y_2$, $Y_3$, $Y_4$, $Y_5$, $Y_6$, $Y_7$, $Y_8$ and $Y_9$ represent a carbon $R_1$, $R_2$, $R_3$, $R_{19}$, $R_{20}$, $R_{21}$, $R_{28}$, $R_{29}$, and $R_{30}$ are selected from the group comprising H, F, Cl, Br, I, $CH_3$, $CF_3$, $NO_2$, OH, tiocyanate, isotiocyanate, —NCO, —CN, CHO, COOH, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, linear or branched, chiral or achiral, from 2 till 18 carbon atom containing any combination of the following groups: $CF_3$, $NO_2$, OH, CHO, COOH, tiocyanate, isotiocyanate, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, aliphatic or alicyclic alkyl, alkenyl, alkynyl, aryl, ester, carboxy, amine, sulfoxide, amide, phosphine or neutral heterocyclic moieties selected from the group comprising ethyl, n-propyl, phosphine, n-Butyl, t-Butyl, iso-Propyl, Hexyl, $F(CF_2)_m(CH_2)_n$— (m=1-10, n=0-4), $F(CF_2)_m(CH_2)_nC_6H_4$— (m=1-10, n=0-4), $O(CH_2CH_2O)_nCH_3$(n=0-10000), haloalkyl, mono- or, disulfide, natural or synthetic sugar residuals, biotin, phosphonium moiety, aminoacidic residual, antibody, Phenyl, Chlorophenyl, Tolyl, Anisyl, Trifluoromethylphenyl, Benzyl, Fluorenyl, Carbazolyl, Cyclohexyl, Menthyl, Allyl, Hydroxyphenyl, Pentaflurophenyl, Carboxyphenyl, Naphthyl, Pyridyl, Furyl, Bis-(trifluoromethyl)-phenyl, Carbene, N-heterocyclic Carbene, Imidazolyl, Pyridazinyl, Pyrazinyl, Pyrimidyl, Phosphinyl, any aromatic rings fused with the central N-containing esatomic ring, selected from the group comprising

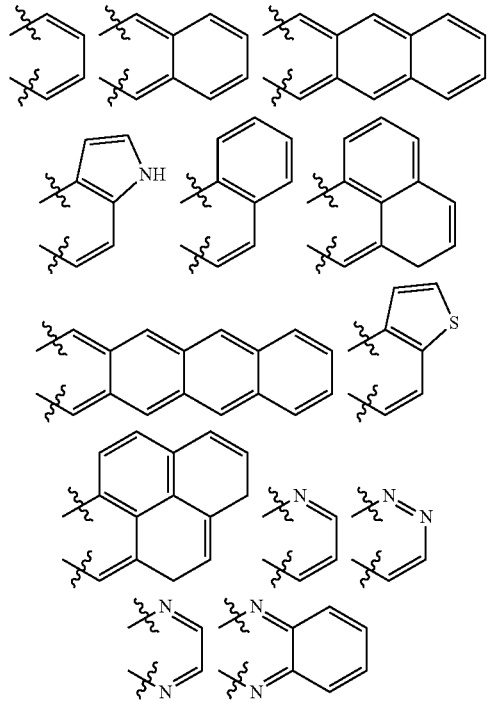

and wherein
$X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$ and $X_{18}$ are carbon and nitrogen atoms, that independently combine in such a way to have heterocycles selected from the group comprising pyrroles, diazoles, triazoles, tetrazoles, and wherein $R_{4-9}$, $R_{22-27}$ or $R_{31-36}$ are selected from the group of mono- or polyatomic substituents, and wherein
the platinum ion is coordinated to a ligand L and/or L' which is neutral, mono- or multi-either positively or negatively charged to yield a neutral-core complex, wherein the molecule is either fully neutral or either positively or negatively charged
as imaging agent comprising the following steps: in vitro or in vivo incubation of cells with the platinum (II) complex and imaging of the platinum (II) complex by fluorescence microscopy.

2. A process of using a platinum (II) complex according to one of formulas (I) or (II)

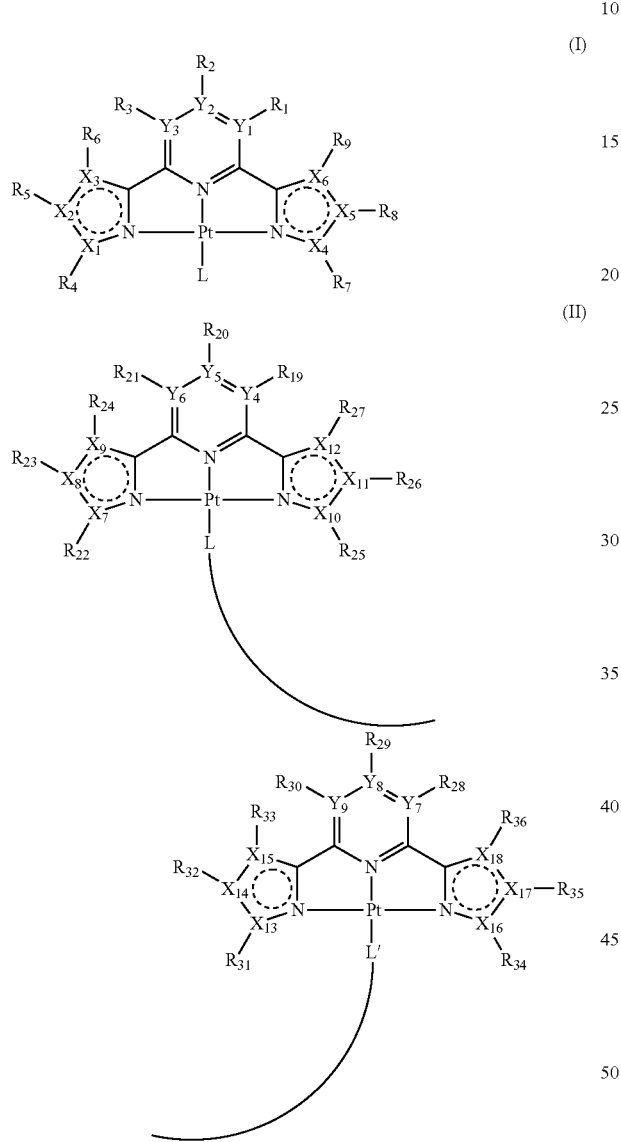

comprising a mono- or dinuclear N^N^N-type ligand wherein $Y_1, Y_2, Y_3, Y_4, Y_5, Y_6, Y_7, Y_8$ and $Y_9$ can be independently either carbon or nitrogen with the proviso if $Y_1$ or $Y_4$ are a nitrogen atom, then $R_1$ or $R_{19}$ are absent;
if $Y_2$ or $Y_5$ are a nitrogen atom, then $R_2$ or $R_{20}$ are absent;
if $Y_3$ or $Y_6$ are a nitrogen atom, then $R_3$ or $R_{21}$ are absent;
if $Y_7$ is a nitrogen atom, then $R_{28}$ is absent;
if $Y_8$ is a nitrogen atom, then $R_{29}$ is absent;
if $Y_9$ is a nitrogen atom, then $R_{30}$ is absent,
and if $Y_1, Y_2, Y_3, Y_4, Y_5, Y_6, Y_7, Y_8$ and $Y_9$ represent a carbon $R_1, R_2, R_3, R_{19}, R_{20}, R_{21}, R_{28}, R_{29}$ and $R_{30}$ are selected from the group comprising H, F, Cl, Br, I, $CH_3$, $CF_3$, $NO_2$, OH, tiocyanate, isotiocyanate, —NCO, —CN, CHO, COOH, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, linear or branched, chiral or achiral, from 2 till 18 carbon atom containing any combination of the following groups: $CF_3$, $NO_2$, OH, CHO, COOH, tiocyanate, isotiocyanate, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, aliphatic or alicyclic alkyl, alkenyl, alkynyl, aryl, ester, carboxy, amine, sulfoxide, amide, phosphine or neutral heterocyclic moieties selected from the group comprising ethyl, n-propyl, phosphine, n-Butyl, t-Butyl, iso-Propyl, Hexyl, $F(CF_2)_m(CH_2)_n$— (m=1-10, n=0-4), $F(CF_2)_m(CH_2)_nC_6H_4$— (m=1-10, n=0-4), $O(CH_2CH_2O)_nCH_3$ (n=0-10000), haloalkyl, mono- or, disulfide, natural or synthetic sugar residuals, biotin, phosphonium moiety, aminoacidic residual, antibody, Phenyl, Chlorophenyl, Tolyl, Anisyl, Trifluoromethylphenyl, Benzyl, Fluorenyl, Carbazolyl, Cyclohexyl, Menthyl, Allyl, Hydroxyphenyl, Pentaflurophenyl, Carboxyphenyl, Naphthyl, Pyridyl, Furyl, Bis-(trifluoromethyl)-phenyl, Carbene, N-heterocyclic Carbene, Imidazolyl, Pyridazinyl, Pyrazinyl, Pyrimidyl, Phosphinyl, any aromatic rings fused with the central N-containing esatomic ring, selected from the group comprising

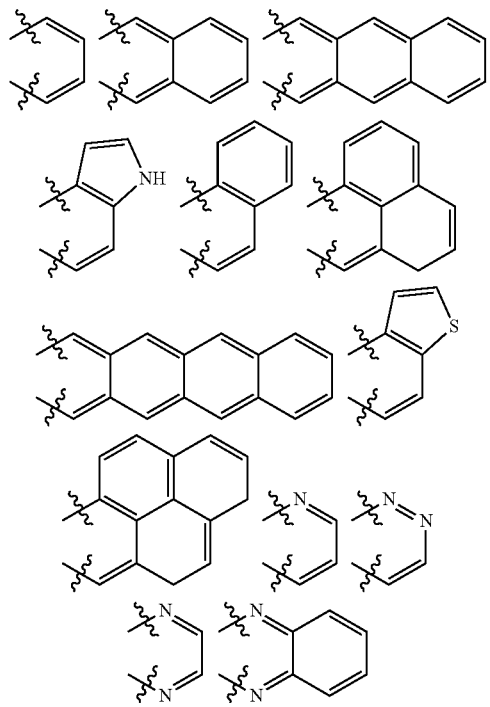

and wherein
$X_1, X_2, X_3, X_4, X_5, X_6, X_7, X_8, X_9, X_{10}, X_{11}, X_{12}, X_{13}, X_{14}, X_{15}, X_{16}, X_{17}$ and $X_{18}$ are carbon and nitrogen atoms, that independently combine in such a way to have heterocycles selected from the group comprising pyrroles, diazoles, triazoles, tetrazoles, and wherein $R_{4-9}$, $R_{22-27}$ or $R_{31-36}$ are selected from the group of mono- or polyatomic substituents, and wherein the platinum ion is coordinated to a ligand L and/or L' which is neutral, mono- or multi-either positively or negatively charged to yield a neutral-core complex, wherein the molecule is either fully neutral or either positively or negatively charged in a detection method for detecting toxic monomers wherein loss of aggregation leads to liberation of toxic monomers.

3. A process of using a platinum (II) complex according to claim 1 or 2, wherein L and/or L' comprise on remote sites —$SO_3^{31}$, —$OSO_3^{31}$, -phosphonium, —$COO^-$, alkylammonium, aminoacid, phosphate.

4. A process of using a platinum (II) complex according to claim 1 or 2, wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$ and $X_{18}$ represent independently from each other a carbon atom and $R_{4-9}$, $R_{22-27}$ or $R_{31-36}$, respectively, are selected from the group comprising H, F, Cl, Br, I, $CH_3$, $CF_3$, $NO_2$, OH, tiocyanate, isotiocyanate, —NCO, —CN, CHO, COOH, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, linear or branched, chiral or achiral, from 2 till 18 carbon atom containing any combination of the following groups: $CF_3$, $NO_2$, OH, CHO, COOH, tiocyanate, isotiocyanate, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, aliphatic or alicyclic alkyl, alkenyl, alkynyl, aryl, ester, carboxy, amine, sulfoxide, amide, phosphine or neutral heterocyclic moieties selected from the group comprising ethyl, n-propyl, phosphine, n-Butyl, t-Butyl, iso-Propyl, Hexyl, $F(CF_2)_m(CH_2)_n$— (m=1-10, n=0-4), $F(CF_2)_m(CH_2)_nC_6H_4$— (m=1-10, n=0-4), $O(CH_2CH_2O)_nCH_3$ (n=0-10000), haloalkyl, mono- or, disulfide, natural or synthetic sugar residuals, biotin, phosphonium moiety, aminoacidic residual, antibody, Phenyl, Chlorophenyl, Tolyl, Anisyl, Trifluoromethylphenyl, Benzyl, Fluorenyl, Carbazolyl, Cyclohexyl, Menthyl, Allyl, Hydroxyphenyl, Pentaflurophenyl, Carboxyphenyl, Naphthyl, Pyridyl, Furyl, Bis-(trifluoromethyl)-phenyl, Carbene, N-heterocyclic Carbene, Imidazolyl, Pyridazinyl, Pyrazinyl, Pyrimidyl, Phosphinyl, any aromatic rings fused with the central N-containing esatomic ring, selected from the group comprising

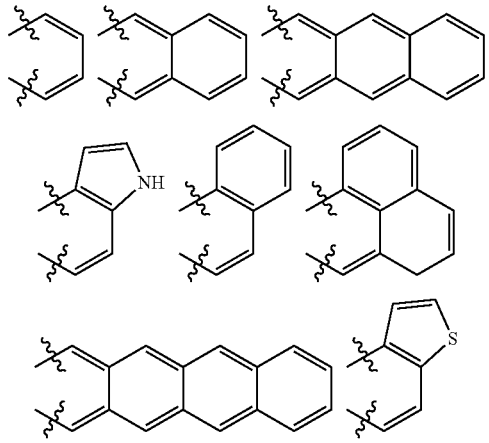

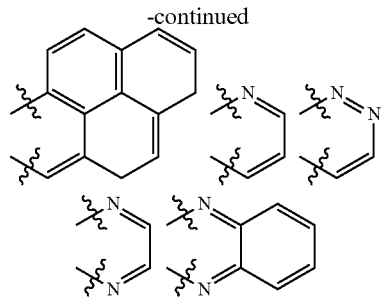

5. A process of using a platinum (II) complex according to claim 1 or 2, wherein in formula (I) the tridentate ligand is dianionic and L is a neutral monodentate ligand coordinating through nitrogen, phosphorus, arsenic, carbon.

6. A process of using a platinum (II) complex according to claim 1 or 2, wherein in formula (I) L coordinates through nitrogen and corresponds to formula (III) or (IV)

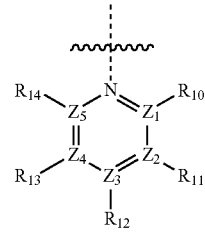

(III)

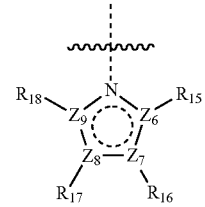

(IV)

wherein $Z_1$, $Z_2$, $Z_3$, $Z_4$, $Z_5$, $Z_6$, $Z_7$, $Z_8$ and $Z_9$ represent independently carbon or nitrogen with the proviso if $Z_1$ is a nitrogen atom, then $R_{10}$ is absent;
if $Z_2$ is a nitrogen atom, then $R_{11}$ is absent;
if $Z_3$ is a nitrogen atom, then $R_{12}$ is absent;
if $Z_4$ is a nitrogen atom, then $R_{13}$ is absent;
if $Z_5$ is a nitrogen atom, then $R_{14}$ is absent;
if $Z_6$ is a nitrogen atom, then $R_{15}$ is absent;
if $Z_7$ is a nitrogen atom, then $R_{16}$ is absent;
if $Z_8$ is a nitrogen atom, then $R_{17}$ is absent;
if $Z_9$ is a nitrogen atom, then $R_{18}$ is absent;

wherein $R_{10}$, $R_{11}$, $R_{12}$, $R_{13}$, $R_{14}$, $R_{15}$, $R_{16}$, $R_{17}$ and $R_{18}$ are selected independently from the group comprising H, F, Cl, Br, I, $CH_3$, $CF_3$, $NO_2$, OH, tiocyanate, isotiocyanate, —NCO,—CN, CHO, COOH, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, linear or branched, chiral or achiral, from 2 till 18 carbon atomcontaininganycombination of the following groups: $CF_3$, $NO_2$, OH, CHO, COOH, tiocyanate, isotiocyanate, keto, amine, mono- or di-alkylamino, mono- or diaryl-amino, alkoxy, heteroaryloxy, alkoxycarbonil, acyloxy, acylamino, mercapto, sulfonylamino, cyano, carbamoyl, sulfonylamino, sulfamoyl, sulfinyl, aliphatic or alicyclic alkyl, alkenyl, alkynyl, aryl, ester, carboxy, amine, sulfoxide, amide, phosphine or neutral heterocyclic moieties selected from the group comprising ethyl, n-propyl, phosphine, n-Butyl, t-Butyl, iso-Propyl, Hexyl, $F(CF_2)_m(CH_2)_n$— (m=1-10, n=0-4), $F(CF_2)_m(CH_2)_n C_6H_4$— (m=1-10, n=0-4), $O(CH_2CH_2O)_nCH_3$ (n=0-10000), haloalkyl, mono- or, isulphide, natural or synthetic sugar residual, biotin, phosphonium moiety, aminoacidic residual, antibody, Phenyl, Chlorophenyl, Tolyl, Anisyl, Trifluoromethylphenyl, Benzyl, Fluorenyl, Carbazolyl, Cyclohexyl, Menthyl, Allyl, Hydroxyphenyl, Pentaflurophenyl, Carboxyphenyl, Naphthyl, Pyridyl, Furyl, Bis-(trifluoromethyl)-phenyl, Carbene, N-heterocyclic Carbene, Imidazolyl, Pyridazinyl, Pyrazinyl, Pyrimidyl, Phosphinyl, any aromatic rings fused with the central N-containing Pt-coordinating ring, selected from the group comprising

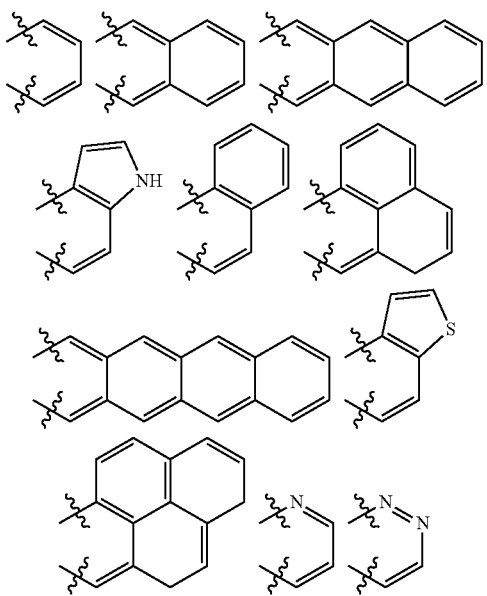

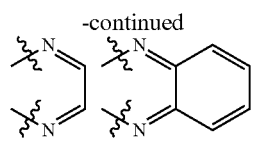

7. A process of using a platinum (II) complex according to claim 1 or 2, wherein in formula (I) L coordinates through phosphorus and L is $PAr_3$, $PR_3$, $P(OR)_3$ and wherein R represents phenyl.

8. A process of using a platinum (II) complex according to claim 1 or 2, wherein in formula (I) L coordinates through arsenic and L is $AsAr_3$.

9. A process of using a platinum (II) complex according to claim 1 or 2, wherein in formula (I) L coordinates through carbon and L is a N-heterocyclic carbene, carbonyl.

10. A process of using a platinum (II) complex according to claim 1 or 2, wherein in formula (I) the tridentate ligand is mono-anionic and L is a mono-anionic ligand selected from the group comprising —Cl, —Br, —I, —CN, —NCS, —NSC, —NCO, —SAr, $NaHPO_4$, $HCO_3$, carboxylate, —OAr, azolates, pyrrolates, ArO.

11. A process of using a platinum (II) complex according to claim 1 or 2, wherein the ligand is covalently bound to biomolecules selected from the group comprising a polypeptide or protein, a nucleoside or a nucleotide chain and a sugar or sugar moiety.

12. A process of using a platinum (II) complex according to claim 1 or 2, wherein the complex is in the aggregated form.

13. A process of using a platinum (II) complex according to claim 12, wherein the emission color or the emission quantum yield or the excited state lifetime change upon aggregation of the complex.

14. A process of using a platinum (II) complex according to claim 11, wherein the complex is coupled to a targeting agent.

* * * * *